US012642480B2

(12) United States Patent
Martinez et al.

(10) Patent No.: US 12,642,480 B2
(45) Date of Patent: Jun. 2, 2026

(54) DYNAMIC INFANT ORAL-MOTOR ASSESSMENT AND FEEDBACK

(71) Applicant: Sipple Care, Inc., Riverside, CT (US)

(72) Inventors: Caroline Martinez, Riverside, CT (US); Vitaly Shlimovich, Rishon LeZion (IL)

(73) Assignee: Simple Care, Inc., Riverside, CT (US)

( * ) Notice: Subject to any disclaimer, the term of this patent is extended or adjusted under 35 U.S.C. 154(b) by 45 days.

(21) Appl. No.: 18/528,591

(22) Filed: Dec. 4, 2023

(65) Prior Publication Data

US 2024/0180480 A1 Jun. 6, 2024

Related U.S. Application Data

(60) Provisional application No. 63/588,892, filed on Oct. 9, 2023, provisional application No. 63/385,927, filed on Dec. 2, 2022.

(51) Int. Cl.
    *A61B 5/00* (2006.01)
    *A61J 11/00* (2006.01)

(52) U.S. Cl.
    CPC .......... *A61B 5/4205* (2013.01); *A61B 5/0002* (2013.01); *A61B 5/0088* (2013.01);
    (Continued)

(58) Field of Classification Search
    CPC ... A61B 5/4205; A61B 5/0002; A61B 5/0088; A61B 5/486; A61B 5/682; A61B 5/7264;
    (Continued)

(56) References Cited

U.S. PATENT DOCUMENTS 9,687,191 B2 * 6/2017 Chau .................... A61B 5/7267
11,487,273 B1 11/2022 Zhao et al.
(Continued)

FOREIGN PATENT DOCUMENTS

CN 114424937 A * 5/2022

OTHER PUBLICATIONS

English Translation of CN 114424937 A (Year: 2022).*
(Continued)

*Primary Examiner* — Serkan Akar
*Assistant Examiner* — Helene Bor
(74) *Attorney, Agent, or Firm* — TORREY PINES LAW GROUP, PC

(57) ABSTRACT

A monitoring device may include a housing with: a first connector that mechanically couples to a baby bottle; and a second connector that mechanically couples to a nipple; a tube having a first opening defined by a first edge proximate to the first connector and a having second opening defined by a second edge proximate to the second connector. Moreover, the housing may include a set of sensors that perform measurements associated with feeding. During operation, the monitoring device may perform the measurements while a baby is performing the feeding, where the measurements are associated with sucking, swallowing and breathing by the baby. Then, the monitoring device may dynamically provide feedback based at least in part on the measurements. For example, the feedback may include: change to the feeding (such as when to dynamically pause the feeding), a change to a size of the nipple or the baby bottle, etc.

20 Claims, 26 Drawing Sheets

(52) U.S. Cl.
CPC .............. *A61B 5/486* (2013.01); *A61B 5/682* (2013.01); *A61B 5/7264* (2013.01); *A61J 11/0075* (2013.01); *A61B 2503/04* (2013.01); *A61B 2562/0204* (2013.01); *A61B 2562/0247* (2013.01)

(58) Field of Classification Search
CPC ........ A61B 2503/04; A61B 2562/0204; A61B 2562/0247; A61J 11/0075
See application file for complete search history.

(56) References Cited

U.S. PATENT DOCUMENTS

| | | | | |
|---|---|---|---|---|
| 2010/0145166 | A1 * | 6/2010 | Pickler | ................... A61B 5/163 600/301 |
| 2011/0087078 | A1 | 4/2011 | Zemel et al. | |
| 2012/0272747 | A1 * | 11/2012 | Sato | ........................ G01F 1/667 73/861.18 |
| 2018/0197629 | A1 * | 7/2018 | Zhou | ...................... G16H 20/60 |
| 2018/0211558 | A1 * | 7/2018 | Lau | ............................ A61J 9/04 |
| 2020/0113788 | A1 | 4/2020 | Lepine | |
| 2021/0350898 | A1 * | 11/2021 | Mason | .............. A63B 24/0062 |

OTHER PUBLICATIONS

I. C. Yadav et al., "Spectral Smoothing by Variationalmode Decomposition and its Effect on Noise and Pitch Robustness of ASR System," 2018 IEEE International Conference on Acoustics, Speech and Signal Processing (ICASSP), Calgary, AB, Canada, 2018, pp. 5629-5633 (Year: 2018).*

Frakking TT et al. Using an Automated Speech Recognition Approach to Differentiate Between Normal and Aspirating Swallowing Sounds Recorded from Digital Cervical Auscultation in Children. Dysphagia. Dec. 2022;37(6):1482-1492 (Year: 2022).*

International Search Report and Written Opinion received in PCT/US2023/082371, mailed on Apr. 15, 2024, 9 pages).

* cited by examiner

MONITORING
DEVICE
500

ADAPTER
542

MONITORING
DEVICE
500

MONITORING
DEVICE
500

ADAPTER
542

MONITORING
DEVICE
500

BOTTLE
910

NIPPLE
1010

MONITORING
DEVICE
1000

BOTTLE
1012

MONITORING
DEVICE
1200

MONITORING
DEVICE
1300

UPPER LID
1416

GASKET
1414

MEMBRANE
1412

INSERT
1410

MONITORING
DEVICE
1400

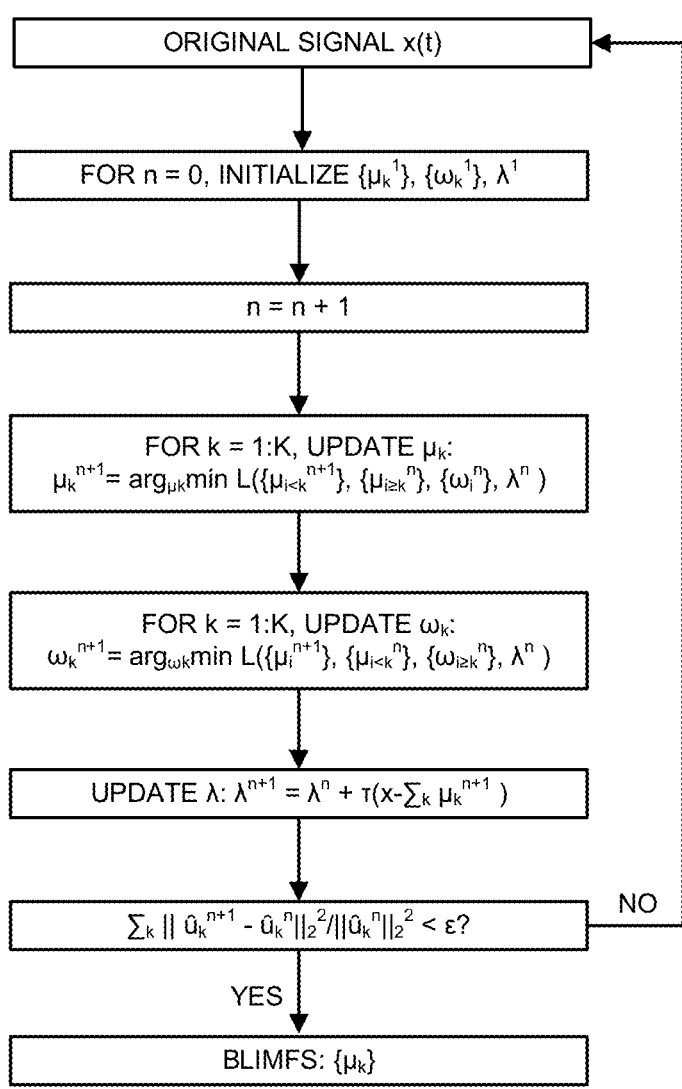

ORIGINAL SIGNAL x(t)

FOR n = 0, INITIALIZE $\{\mu_k^1\}$, $\{\omega_k^1\}$, $\lambda^1$ n = n + 1

FOR k = 1:K, UPDATE $\mu_k$:
$\mu_k^{n+1} = \arg_{\mu_k}\min L(\{\mu_{i<k}^{n+1}\}, \{\mu_{i\geq k}^n\}, \{\omega_i^n\}, \lambda^n)$ FOR k = 1:K, UPDATE $\omega_k$:
$\omega_k^{n+1} = \arg_{\omega_k}\min L(\{\mu_i^{n+1}\}, \{\mu_{i<k}^n\}, \{\omega_{i\geq k}^n\}, \lambda^n)$ UPDATE $\lambda$: $\lambda^{n+1} = \lambda^n + \tau(x - \sum_k \mu_k^{n+1})$ $\sum_k \|\hat{u}_k^{n+1} - \hat{u}_k^n\|_2^2 / \|\hat{u}_k^n\|_2^2 < \varepsilon$?    NO

YES

BLIMFS: $\{\mu_k\}$

FIG. 22

DYNAMIC INFANT ORAL-MOTOR ASSESSMENT AND FEEDBACK

CROSS REFERENCE TO RELATED APPLICATIONS

This application claims priority under 35 U.S.C. 119(e) to: U.S. Provisional Application Ser. No. 63/588,892, "Dynamic Infant Oral-Motor Assessment and Feedback," filed on Oct. 9, 2023, by Caroline Martinez et al.; and U.S. Provisional Application Ser. No. 63/385,927, "Dynamic Infant Oral-Motor Assessment and Feedback," filed on Dec. 2, 2022, by Caroline Martinez et al., the contents of both which are herein incorporated by reference.

FIELD

The described embodiments relate to providing feedback regarding infant feeding. Notably, the described embodiments relate to dynamic infant oral-motor assessment and feedback regarding infant feeding.

BACKGROUND

Many babies refuse feeding bottles or frequently display conflicted feeding behaviors because of an inability to suck or swallow properly. These feeding problems can be caused by a variety of factors, including incorrect positioning of a bottle, using the wrong sized nipple, having a flow rate that is too high, etc. Moreover, feeding problems may be exacerbated when a baby or an infant is born premature or has a medical condition that causes dysfunctional or disorganized feeding. Furthermore, if not properly addressed, dysfunctional oral motor strength and coordination can lead to health risks and may also contribute to cascading negative effects on feeding, speech and social-emotional bonding foundations.

In order to help parents identify appropriate corrective action(s) and to help parents and their babies learn appropriate skills and feeding techniques, feeding consultants and medical professionals typically need to assess the various factors that can contribute to feeding problems. However, it is often challenging to collect and analyze objective information during feeding between medical appointments.

SUMMARY

In a first group of embodiments, a monitoring device is described. This monitoring device includes a housing with: a first connector that mechanically couples to a baby bottle; and a second connector that mechanically couples to a nipple; a tube having a first opening defined by a first edge proximate to the first connector and a having second opening defined by a second edge proximate to the second connector. Moreover, the housing includes a set of sensors that perform measurements associated with feeding. During operation, the monitoring device performs the measurements while a baby is performing the feeding, where the measurements are associated with sucking, swallowing and breathing by the baby. Then, the monitoring device dynamically provides feedback based at least in part on the measurements, where the feedback includes: when to dynamically pause the feeding, a change to a flow rate during the feeding, a change to a size of the nipple, a change to a size of the baby bottle, a change to promote stronger sucking by the baby, a change to an anatomical position of the baby during the feeding, a recommendation for a swallowing study, a recommendation for the baby to use a pacifier between instances of the feeding, diagnostic information about a possible (such as presence of or a risk of) tongue-tie, diagnostic information about possible excessive air swallowing into the stomach and/or a recommendation for additional therapy for the baby.

For example, the feedback may include: signals or instructions to guide a feeder to regulate a number of sucks per burst (or sequence of swallows), a respiratory rate and/or a duration of bursts and pauses or time intervals between swallows (where the duration is sometimes referred to as 'pacing') by adjusting a flow rate dial (e.g., if the flow rate is too fast) and/or an angle of the baby bottle.

Note that the feedback may be based at least in part on a modal decomposition of the measurements (such as variational mode decomposition or VMD of the measurements) and/or a pretrained analysis model (such as a neural network).

Furthermore, the monitoring device may include an interface circuit that wirelessly communicates with an electronic device, which is separate from the monitoring device. During operation, the monitoring device may provide, addressed to the electronic device, information associated with the measurements. Next, the monitoring device may receive the feedback associated with the electronic device.

Additionally, the feedback may include information a quality of the feeding while the baby is feeding.

In some embodiments, the measurements are non-invasive and are performed without the sensors being placed in a mouth of the baby.

Note that the set of sensors may include two or more sensors. For example, the set of sensors may include: a pressure sensor, an acoustic sensor, an accelerometer, a light detection and ranging (LiDAR) sensor and/or an infrared sensor.

Moreover, the measurements may correspond to one or more oral-motor metrics associated with the baby. For example, the one or more oral-motor metrics may include: tongue kinetics (such as tongue movement), a force of sucking, a suction and expression pressure, the flow rate, a sucking/swallowing/breathe ratio, micro-gagging, a pressure of lip seal, a pressure of tongue, and/or distance from monitoring device to a top of a fluid level line in the baby bottle.

Furthermore, the monitoring device may include an integrated circuit that analyzes the measurements and/or determines the feedback. In some embodiments, the analysis may include computing the one or more oral-motor metrics based at least in part on the measurements. Alternatively or additionally, the feedback may include the one or more oral-motor metrics. For example, the monitoring device may provide diagnostic information associated with feeding/oromotor difficulties based at least in part on the analysis of the measurements and/or the one or more oral-motor metrics. Note that the diagnostic information may include: a feeding performance score or a risk score. Moreover, the diagnostic information may include or may correspond to: possible developmental delays, the possible tongue-tie, and/or possible feeding difficulties. In some embodiments, the possible feeding difficulties may include: reflux, colic, the excessive air swallowing into the stomach and/or a type of oral-motor functional impairment.

Additionally, the monitoring device may compute and/or the feedback may include one or more feeding quality metrics based at least in part on the analysis and/or the one or more oral-motor metrics, where the one or more feeding quality metrics may include: oral pressure, feeding consistency, and/or a sucking/swallowing/breath rate. In some embodiments, the monitoring device may compute and/or the feedback may include a normalized maturity index based at least in part on the analysis, the one or more oral-motor metrics and/or the one or more feeding quality metrics, which may include indices of disordered feeding. Note that the normalized maturity index corresponds to a ratio of a developmental metrics of the baby and a chronological age of the baby.

Another embodiment provides the electronic device.

Another embodiment provides a computer-readable storage medium for use with the monitoring device or the electronic device. When executed by the monitoring device or the electronic device, this computer-readable storage medium causes the monitoring device or the electronic device to perform at least some of the aforementioned operations.

Another embodiment provides a method, which may be performed by the monitoring device or the electronic device. This method includes at least some of the aforementioned operations.

In a second group of embodiments, an electronic device is described. This electronic device includes: a display; a processor coupled to the display; and memory coupled to the processor and that stores program instructions, where, when executed by the processor cause the electronic device to perform operations. Notably, during operation, the electronic device: generates a user interface; and displays, on the display, the user interface. This user interface may include information that specifies dynamic feedback associated with feeding by a baby using a baby bottle, where the feedback is based at least in part on analysis of measurements performed while the baby is performing the feeding.

Note that the feedback may include: when to dynamically pause the feeding (e.g., to ensure adequate respiration), a change to a flow rate during the feeding, a change to a size of the nipple used during the feeding (e.g., for improved or optimal latching), a change to a size of the baby bottle during the feeding, a change to promote stronger sucking by the baby, a change to an anatomical position of the baby during the feeding, a recommendation for a swallowing study, a recommendation for the baby to use a pacifier between instances of the feeding, diagnostic information about a possible tongue-tie, diagnostic information about possible excessive air swallowing into the stomach and/or a recommendation for additional therapy for the baby.

Moreover, the feedback may be based at least in part on a modal decomposition of the measurements (such as VMD of the measurements) and/or a pretrained analysis model (such as a neural network).

Furthermore, the electronic device may include an interface circuit that communicates with a monitoring device, which is separate from the electronic device. This monitoring device may be mechanically coupled to the baby bottle and the nipple. During operation, the electronic device may receive the measurements and/or one or more oral-motor metrics associated with the baby and corresponding to the measurements from the monitoring device. Alternatively or additionally, the interface circuit may communicate with a computer system that is separate from the electronic device, and the electronic device may receive the feedback associated with the computer system. In some embodiments, the interface circuit may provide at least some of the feedback to the monitoring device.

For example, at least some of the feedback provided to the monitoring device may correspond to or may include: signals or instructions to guide a feeder to regulate a number of sucks per burst (or sequence of swallows), a respiratory rate and/or a duration of bursts and pauses or time intervals between swallows by adjusting a flow rate dial and/or an angle of the baby bottle.

Additionally, the feedback may include information a quality of the feeding while the baby is feeding. Note that the feedback may be provided while the baby is performing the feeding.

In some embodiments, the measurements may correspond to the one or more oral-motor metrics associated with the baby. For example, the one or more oral-motor metrics may include: tongue kinetics, a force of sucking, a suction and expression pressure, a flow rate, a sucking/swallowing/breathe ratio, micro-gagging, a pressure of lip seal, a pressure of tongue, and/or distance from the monitoring device to a top of a fluid level line in the baby bottle.

Moreover, the electronic device may include an integrated circuit that analyzes the measurements and/or determines the feedback. In some embodiments, the analysis may include computing the one or more oral-motor metrics based at least in part on the measurements. Alternatively or additionally, the feedback may include the one or more oral-motor metrics. For example, the electronic device may provide diagnostic information associated with feeding/oromotor difficulties based at least in part on the analysis of the measurements and/or the one or more oral-motor metrics. Note that the diagnostic information may include: a feeding performance score or a risk score. Furthermore, the diagnostic information may include or may correspond to: possible developmental delays, the possible tongue-tie, and/or possible feeding difficulties. In some embodiments, the possible feeding difficulties may include: reflux, colic, the excessive air swallowing into the stomach and/or a type of oral-motor functional impairment.

Additionally, the electronic device may compute and/or the feedback may include one or more feeding quality metrics based at least in part on the analysis and/or the one or more oral-motor metrics, where the one or more feeding quality metrics may include: oral pressure, feeding consistency, and/or a sucking/swallowing/breath rate. In some embodiments, the electronic device may compute and/or the feedback may include a normalized maturity index based at least in part on the analysis, the one or more oral-motor metrics and/or the one or more feeding quality metrics, which may include indices of disordered feeding. Note that the normalized maturity index corresponds to a ratio of a developmental metrics of the baby and a chronological age of the baby.

Note that the user interface may include one or more graphs of the feedback, analysis results and/or the one or more oral-motor metrics.

Another embodiment provides the monitoring device.

Another embodiment provides a computer-readable storage medium for use with the monitoring device or the electronic device. When executed by the monitoring device or the electronic device, this computer-readable storage medium causes the monitoring device or the electronic device to perform at least some of the aforementioned operations.

Another embodiment provides a method, which may be performed by the monitoring device or the electronic device. This method includes at least some of the aforementioned operations.

This Summary is provided for purposes of illustrating some exemplary embodiments, so as to provide a basic understanding of some aspects of the subject matter described herein. Accordingly, it will be appreciated that the above-described features are examples and should not be construed to narrow the scope or spirit of the subject matter described herein in any way. Other features, aspects, and advantages of the subject matter described herein will become apparent from the following Detailed Description, Figures, and Claims.

BRIEF DESCRIPTION OF THE FIGURES

FIG. 22 is a flow diagram illustrating an example of a variational mode decomposition (VMD) technique in accordance with an embodiment of the present disclosure.

6

Figure 23:
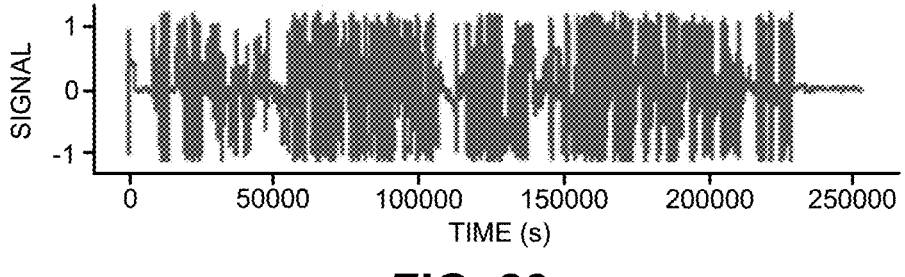
FIG. 23 is a drawing illustrating an example of acoustic measurements during feeding in accordance with an embodiment of the present disclosure.
Figure 24:
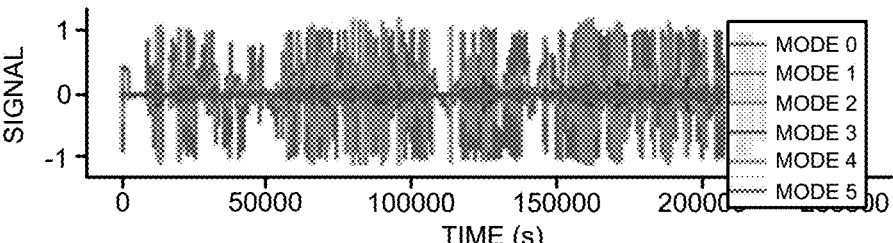

FIG. 24 is a drawing illustrating an example of VMD of the acoustic measurements in FIG. 23 in accordance with an embodiment of the present disclosure.

Figure 25:
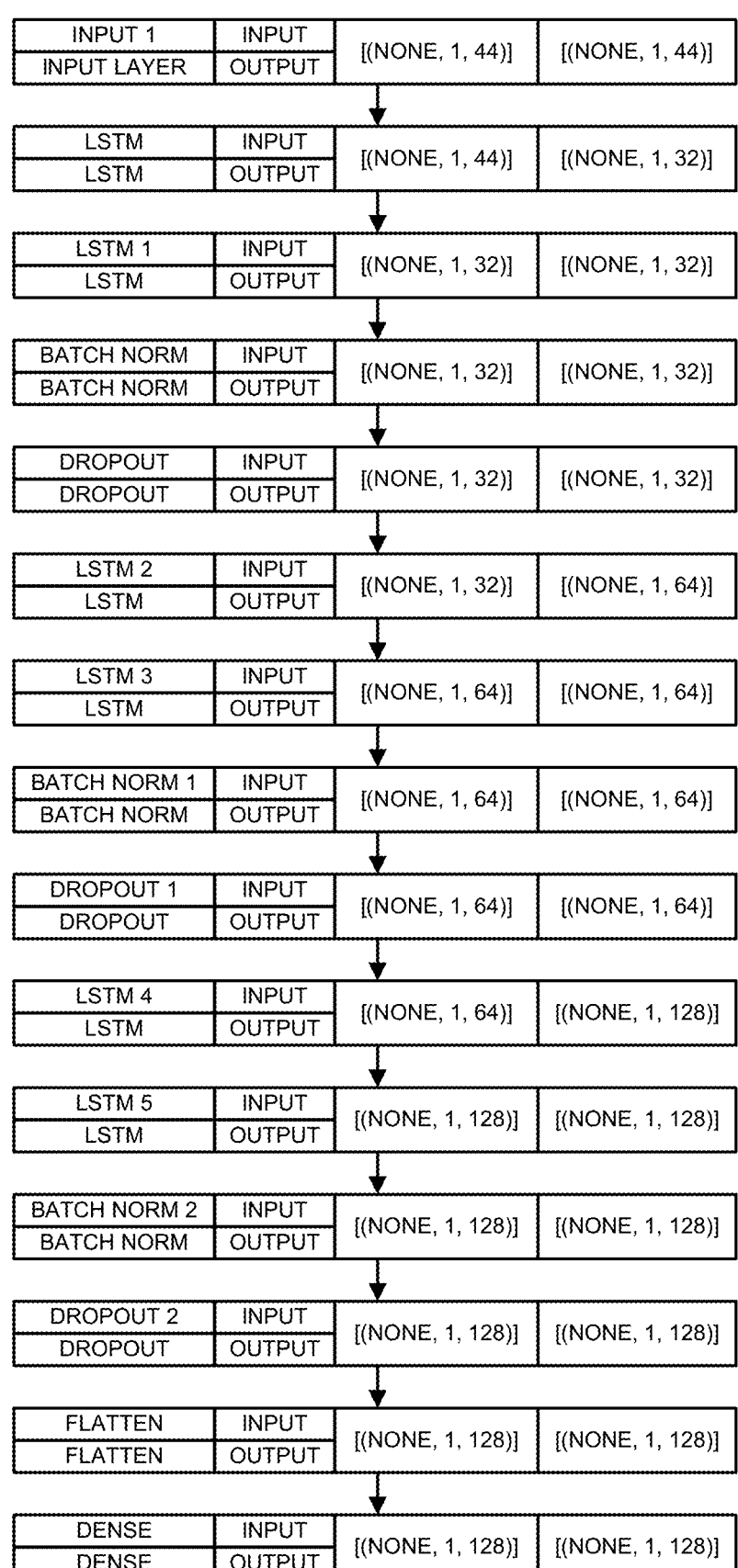

FIG. 25 is a drawing illustrating an example of a neural network in accordance with an embodiment of the present disclosure.

Figure 26:
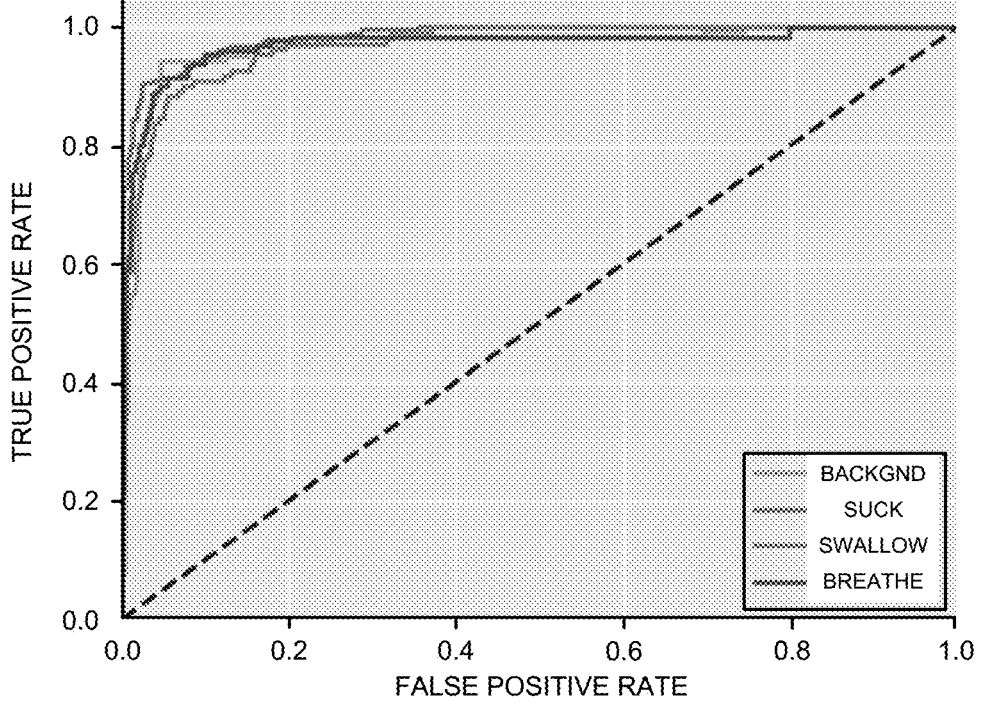

FIG. 26 is a drawing illustrating an example of receiver operator characteristics for the neural network of FIG. 25 in accordance with an embodiment of the present disclosure.

Figure 27:
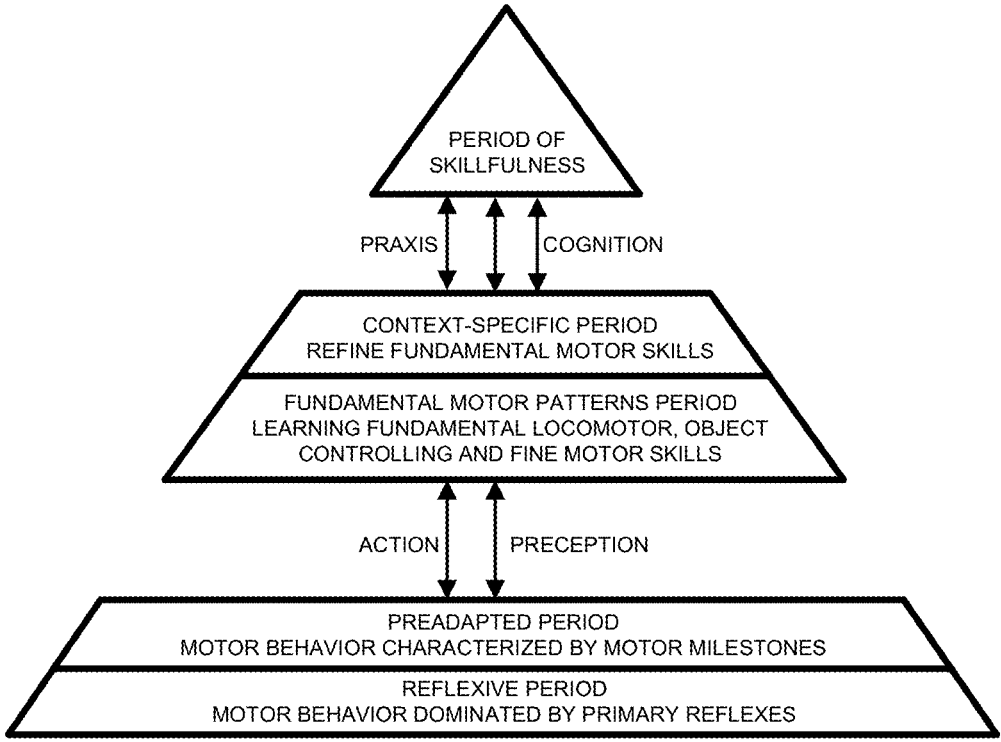

FIG. 27 is a drawing illustrating an example of variation in oral-motor behavior during development in accordance with an embodiment of the present disclosure.

Figure 28:
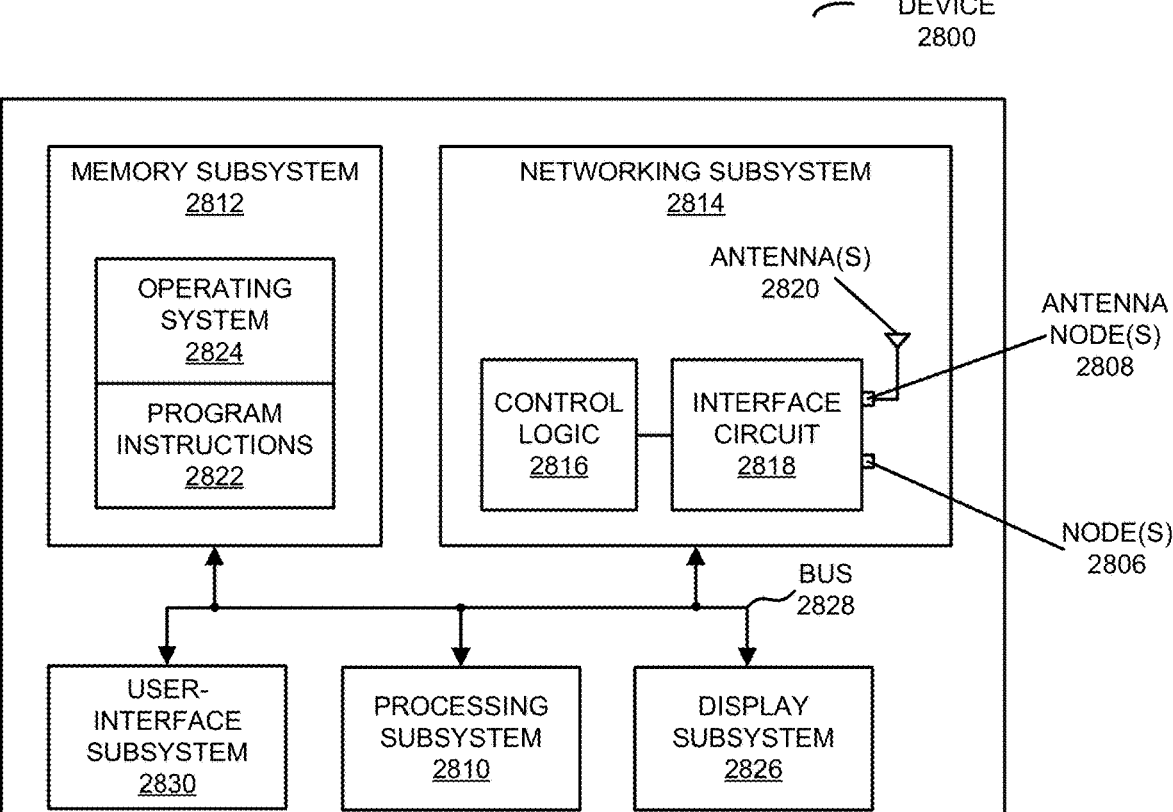

FIG. 28 is a block diagram illustrating an example of an electronic device in accordance with an embodiment of the present disclosure.

Note that like reference numerals refer to corresponding parts throughout the drawings. Moreover, multiple instances of the same part are designated by a common prefix separated from an instance number by a dash.

DETAILED DESCRIPTION

A monitoring device is described. This monitoring device may include a housing with: a first connector that mechanically couples to a baby bottle; and a second connector that mechanically couples to a nipple; a tube having a first opening defined by a first edge proximate to the first connector and a having second opening defined by a second edge proximate to the second connector. Moreover, the housing may include a set of sensors that perform measurements associated with feeding. During operation, the monitoring device may perform the measurements while a baby is performing the feeding, where the measurements are associated with sucking, swallowing and breathing by the baby. Then, the monitoring device may dynamically provide feedback based at least in part on the measurements. For example, the feedback may include: when to dynamically pause the feeding, a change to a flow rate during the feeding, a change to a size of the nipple, a change to a size of the baby bottle, a change to promote stronger sucking by the baby, a change to an anatomical position of the baby during the feeding, a recommendation for a swallowing study, a recommendation for the baby to use a pacifier between instances of the feeding, diagnostic information about a possible tongue-tie, diagnostic information about possible excessive air swallowing into the stomach and/or a recommendation for additional therapy for the baby.

By performing the measurements and providing the feedback, these monitoring techniques may facilitate monitoring of feeding in real-world conditions. For example, the monitoring device may allow parents to monitor a baby's feeding while they are at home and without adversely impacting measurements. Moreover, the monitoring may be performed whenever a baby is feed using a bottle, which may provide more-frequent data. The improved data quality and the increased sampling frequency may facilitate improved feedback and/or more accurate diagnostic information about potential medical conditions. Furthermore, the monitoring techniques may provide real-time feedback during feeding that helps parents identify and take appropriate corrective action(s) and that helps parents and their babies learn appropriate skills and feeding techniques. This may enable treatment of feeding difficulties and may ensure prevention of feeding aversions as parents are able to read and respond to babies' cues. Additionally, the information collected and/or determined by the monitoring device (or an associated electronic device, such as a computer or a cellular telephone) may help feeding consultants and medical professionals assist the parents, diagnose medical condition(s) and/or determine when additional therapy (such as treatment(s) or intervention(s)) are needed. Consequently, the monitoring techniques may assist parents and feeding consultants and medical professionals, and may improve the health and well-being of babies.

In the discussion that follows, electronic devices, computers and/or servers (which may be local or remotely located from each other) may communicate packets or frames in accordance with a wired communication protocol and/or a wireless communication protocol. The wireless communication protocol may include: a wireless communication protocol that is compatible with an Institute of Electrical and Electronics Engineers (IEEE) 802.11 standard (which is sometimes referred to as 'Wi-Fi®,' from the Wi-Fi Alliance of Austin, Texas), Bluetooth, Bluetooth low energy, a cellular-telephone network or data network communication protocol (such as a third generation or 3G communication protocol, a fourth generation or 4G communication protocol, e.g., Long Term Evolution or LTE (from the 3rd Generation Partnership Project of Sophia Antipolis, Valbonne, France), LTE Advanced or LTE-A, a fifth generation or 5G communication protocol, or other present or future developed advanced cellular communication protocol), and/or another type of wireless interface (such as another wireless-local-area-network interface). For example, an IEEE 802.11 standard may include one or more of: IEEE 802.11a, IEEE 802.11b, IEEE 802.11g, IEEE 802.11-2007, IEEE 802.11n, IEEE 802.11-2012, IEEE 802.11-2016, IEEE 802.11ac, IEEE 802.11ax, IEEE 802.11ba, IEEE 802.11be, or other present or future developed IEEE 802.11 technologies. Moreover, the wired communication protocol may include a wired communication protocol that is compatible with an IEEE 802.3 standard (which is sometimes referred to as 'Ethernet'), e.g., an Ethernet II standard. However, a wide variety of communication protocols may be used. In the discussion that follows, Bluetooth and Ethernet are used as illustrative examples.

Figure 1:
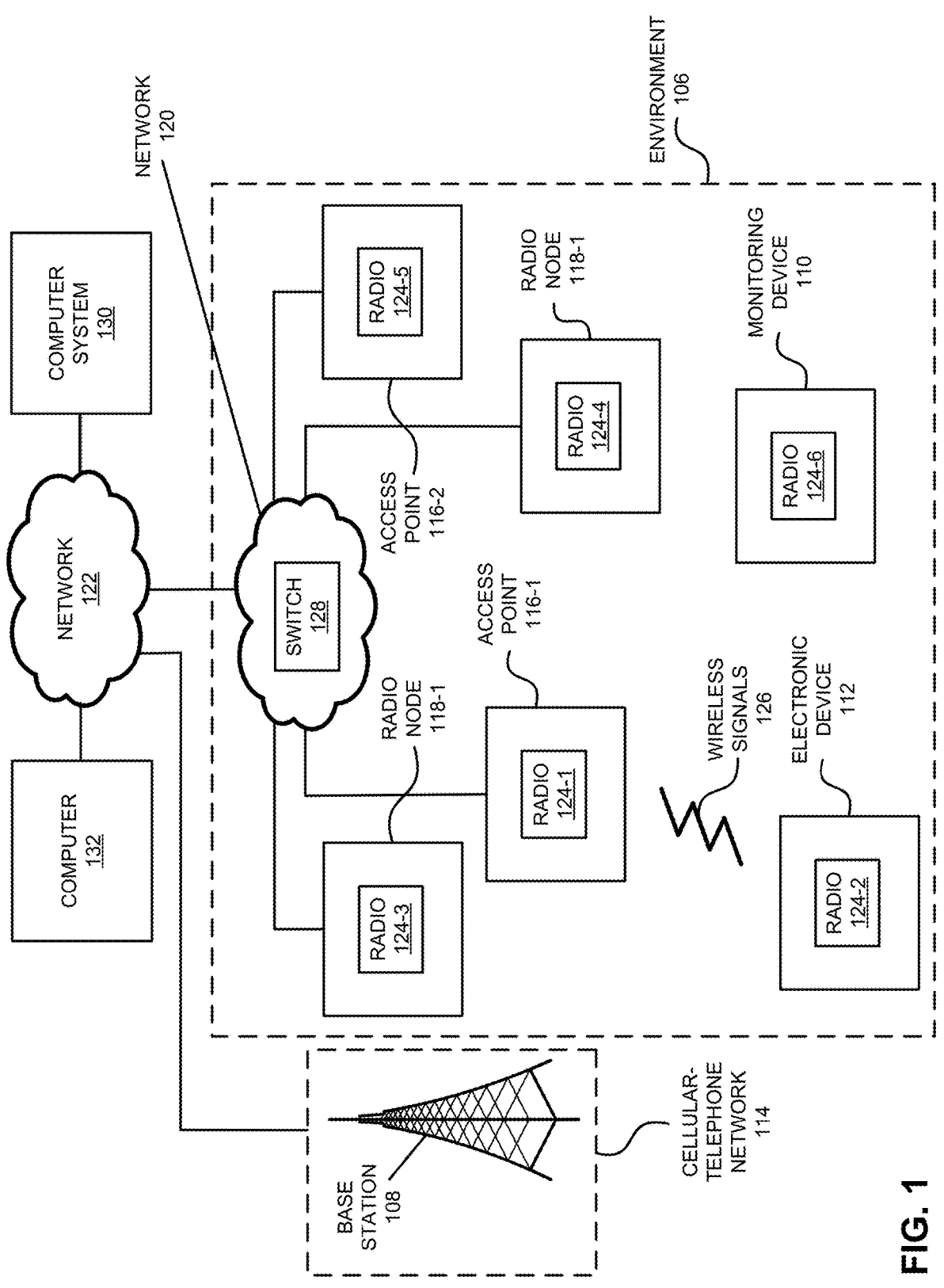
FIG. 1 is a block diagram illustrating an example of a monitoring device and an electronic device in accordance with an embodiment of the present disclosure.

We now describe some embodiments of the monitoring techniques. FIG. 1 presents a block diagram illustrating an example of communication between a monitoring device 110 and an electronic device 112 (such as a cellular telephone, a portable electronic device, or another type of electronic device, etc.) in accordance with an embodiment of the present disclosure. Moreover, electronic device 112 may optionally communicate via a cellular-telephone network 114 (which may include a base station 108), one or more access points 116 (which may communicate using Wi-Fi) in a wireless local area network (WLAN) and/or radio node 118 (which may communicate using LTE) in a small-scale network (such as a small cell). For example, radio node 118 may include: an Evolved Node B (eNodeB), a Universal Mobile Telecommunications System (UMTS) NodeB and radio network controller (RNC), a New Radio (NR) gNB or gNodeB (which communicates with a network with a cellular-telephone communication protocol that is other than LTE), etc. In the discussion that follows, an access point, a radio node or a base station are sometimes referred to generically as a 'communication device.' Moreover, one or more base stations (such as base station 108), access points 116, and/or radio node 118 may be included in one or more networks, such as: a WLAN, a small cell, a local area network (LAN) and/or a cellular-telephone network. In some embodiments, access points 116 may include a physical access point and/or a virtual access point that is implemented in software in an environment of an electronic device or a computer.

Furthermore, electronic device 112 may optionally communicate with computer system 130 (which may include one or more computers or servers, and which may be implemented locally or remotely to provide storage and/or analysis services) using a wired communication protocol (such as Ethernet) via network 120 and/or 122. Note that networks 120 and 122 may be the same or different networks. For example, networks 120 and/or 122 may be a LAN, an intra-net or the Internet. In some embodiments, the wired communication protocol may include a secured connection over transmission control protocol/Internet protocol (TCP/IP) using hypertext transfer protocol secure (HTTPS) with a JavaScript object notation (JSON) Web services connection. Additionally, in some embodiments, network 120 may include one or more routers and/or switches (such as switch 128).

Electronic device 112 and/or computer system 130 may implement at least some of the operations in the monitoring techniques. Notably, as described further below, electronic device 112 and/or computer system 130 may optionally perform at least some of the analysis of measurement data acquired by monitoring device 110, and may optionally provide feedback information to monitoring device 110.

As described further below with reference to FIG. 28, base station 108, monitoring device 110, electronic device 112, access points 116, radio node 118, switch 128 and/or computer system 130 may include subsystems, such as a networking subsystem, a memory subsystem and a processor subsystem. In addition, monitoring device 110, electronic device 112, access points 116 and radio node 118 may include radios 124 in the networking subsystems. More generally, monitoring device 110, electronic device 112, access points 116 and radio node 118 can include (or can be included within) any electronic devices with the networking subsystems that enable monitoring device 110, electronic device 112, access points 116 and radio node 118 to wirelessly communicate with one or more other electronic devices. This wireless communication can comprise transmitting access on wireless channels to enable electronic devices to make initial contact with or detect each other, followed by exchanging subsequent data/management frames (such as connection requests and responses) to establish a connection, configure security options, transmit and receive frames or packets via the connection, etc.

During the communication in FIG. 1, base station 108, monitoring device 110, electronic device 112, access points 116, radio node 118 and/or computer system 130 may wired or wirelessly communicate while: transmitting access requests and receiving access responses on wired or wireless channels, detecting one another by scanning wireless channels, establishing connections (for example, by transmitting connection requests and receiving connection responses), and/or transmitting and receiving frames or packets (which may include information as payloads).

As can be seen in FIG. 1, wireless signals 126 (represented by a jagged line) may be transmitted by radios 124 in, e.g., access points 116 and/or radio node 118 and monitoring device 110 or electronic device 112. For example, radio 124-1 in access point 116-1 may transmit information (such as one or more packets or frames) using wireless signals 126. These wireless signals are received by radio 124-2 in electronic device 112. This may allow access point 116-1 to communicate information to other access points 116 and/or electronic device 112. Note that wireless signals 126 may convey one or more packets or frames.

In the described embodiments, processing a packet or a frame in one or more electronic devices in monitoring device 110, electronic device 112, access points 116, radio node 118 and/or computer system 130 may include: receiving the wireless or electrical signals with the packet or the frame; decoding/extracting the packet or the frame from the received wireless or electrical signals to acquire the packet or the frame; and processing the packet or the frame to determine information contained in the payload of the packet or the frame.

Note that the wired and/or wireless communication in FIG. 1 may be characterized by a variety of performance metrics, such as: a data rate for successful communication (which is sometimes referred to as 'throughput'), an error rate (such as a retry or resend rate), a mean-squared error of equalized signals relative to an equalization target, intersymbol interference, multipath interference, a signal-to-noise ratio, a width of an eye pattern, a ratio of number of bytes successfully communicated during a time interval (such as 1-10 s) to an estimated maximum number of bytes that can be communicated in the time interval (the latter of which is sometimes referred to as the 'capacity' of a communication channel or link), and/or a ratio of an actual data rate to an estimated data rate (which is sometimes referred to as 'utilization'). While instances of radios 124 are shown in components in FIG. 1, one or more of these instances may be different from the other instances of radios 124.

In some embodiments, wireless communication between components in FIG. 1 uses one or more bands of frequencies, such as: 900 MHZ, 2.4 GHz, 5 GHZ, 6 GHz, 7 GHz, 60 GHz, the Citizens Broadband Radio Spectrum or CBRS (e.g., a frequency band near 3.5 GHZ), and/or a band of frequencies used by LTE or another cellular-telephone communication protocol or a data communication protocol. Note that the communication between electronic devices may use multi-user transmission (such as orthogonal frequency division multiple access or OFDMA) and/or multiple-input multiple-output (MIMO).

Although we describe the network environment shown in FIG. 1 as an example, in alternative embodiments, different numbers or types of electronic devices may be present. For example, some embodiments comprise more or fewer electronic devices. As another example, in another embodiment, different electronic devices are transmitting and/or receiving packets or frames.

While FIG. 1 illustrates computer system 130 at a particular location, in other embodiments at least a portion of computer system 130 is implemented at more than one location. Thus, in some embodiments, computer system 130 is implemented in a centralized manner, while in other embodiments at least a portion of computer system 130 is implemented in a distributed manner.

As discussed previously, many babies do not take to a bottle right away or may not suck or swallow properly. Moreover, it is often difficult to obtain information during feeding without disrupting the feeding process. For example, performing measurements during feeding using sensors that are at least partially in the baby's mouth (such as in the nipple of a baby bottle) can adversely impact tongue kinetics, a pressure of lip seal, a pressure of tongue, etc. Therefore, such invasive measurements can exacerbate feeding problems and may degrade the quality of the measurements, which may make it more difficult to: provide feedback on appropriate corrective action(s) (such as appropriate skills and feeding techniques); diagnose potential medical conditions; and/or determine when additional therapies or interventions are needed.

As described further below with reference to FIGS. 2-27, in order to address these challenges, a monitoring device 110 with one or more sensors may be attached or mechanically coupled to a baby bottle. For example, as shown in FIGS. 5-9 and 10-14, embodiments of the monitoring device may be remateably mechanically coupled to a baby bottle and a nipple. Moreover, the one or more sensors in monitoring device 110 may collect or measure data during feeding, such as while a baby is in an environment 106, such as a home, a car, an office and, more generally, in a non-clinical setting. These measurements may be performed in a non-invasive manner. Notably, the one or more sensors may or may not be placed in a mouth of the baby. In some embodiments, the one or more sensors may include: a pressure sensor (which may measure the pressure from a baby's mouth), an acoustic sensor (which may measure sound having frequencies in an acoustic band of frequencies, such as between at least 50-20,000 Hz), an accelerometer (which may measure vibration, motion and/or orientation, such as an inertial sensor), a radar sensor, a LiDAR sensor, a vibration sensor, an infrared sensor (which measures electromagnetic waves in an infrared spectrum, e.g., wavelengths between 700 nm and 1 mm), an imaging sensor (which measures electromagnetic waves in a visible spectrum, e.g., wavelengths between 400 and 700 nm), a flow sensor, a temperature sensor, an orientation sensor (which may measure a bottle angle), a motion sensor, a pulse oximeter (such as using a photoplethysmogram), a force sensing resistor sensor (which may be used to measure tongue pressure and, more generally, a baby's interaction with the nipple) and/or another type of sensor. For example, an infrared sensor or an image sensor may detect a volume of liquid in a bottle.

Furthermore, the measurements may correspond to one or more oral-motor metrics associated with the baby when the baby is feeding (and, more generally, one or more physiological parameters). For example, the one or more oral-motor metrics may include: tongue kinetics (such as a baby using the tongue to protect the back of the throat), a force of sucking, a suction and expression pressure, a flow rate, a sucking/swallowing/breathe ratio, micro-gagging, a pressure of lip seal, a pressure of tongue, and/or distance from monitoring device to a top of a fluid level line.

In the monitoring techniques, the measurements may be analyzed to determine additional information, such as the one or more oral-motor metrics. This analysis may, at least in part, be performed locally (e.g., by monitoring device 110), remotely (e.g., by electronic device 112 and/or computer system 130), or jointly by monitoring device 110, electronic device 112 and/or computer system 130. For example, monitoring device 110 may provide information specifying the measurements via Bluetooth or Bluetooth low energy to electronic device 112. Then, electronic device 112 may analyze the information, such as computing at least one of the one or more oral-motor metrics. Alternatively or additionally, after receiving the information specifying the measurements, electronic device 112 may provide, via networks 120 and 122, the information to computer system 130, which may analyze the information, such as computing at least one of the one or more oral-motor metrics. As noted previously, the communication among monitoring device 110, electronic device 112 and/or computer system 130 may be secure (e.g., encrypted and/or via a tunnel) in order to protect personal and/or medical information.

After performing at least part of the analysis, electronic device 112 and/or computer system 130 may provide, to monitoring device 110, analysis results (such as at least one of the one or more oral-motor metrics) and/or dynamic feedback based at least in part on the one or more oral-motor metrics and, more generally, analysis of the measurements. For example, the feedback may include or may correspond to: a quality of the feeding (where the quality of the feeding is sometimes indicated by one or more 'feedback quality metrics'), when to dynamically pause the feeding, a change to a flow rate during the feeding, a change to nipple size to be used during the current or subsequent feeding, a change to a size of the baby bottle, a change to promote stronger sucking by the baby, a change to an anatomical position of the baby during the feeding, a recommendation for a swallowing study, a recommendation for the baby to use a pacifier between instances of the feeding, a potential medical condition (and, more generally, diagnostic information, such as about a possible tongue-tie or possible excessive air swallowing into the stomach) and/or a recommendation for additional remedial action (such as additional therapy, e.g., treatment(s) or intervention(s)). Alternatively or additionally, monitoring device 110 may determine the feedback based at least in part on the one or more oral-motor metrics and, more generally, analysis of the measurements.

After determining or receiving the analysis results and/or the feedback, monitoring device 110 and/or electronic device 112 may provide information corresponding to the analysis results and/or the feedback while the baby is feeding and/or at another time (such as when the baby is not feeding). For example, electronic device 112 may display a user interface information (such as one or more tables or graphs) corresponding to the measurements, the analysis results, the feedback, and/or additional information (such as diagnostic information, one or more feeding quality metrics, etc.).

Alternatively or additionally, monitoring device 110 may provide information corresponding to the feedback, such as signals (e.g., selectively illuminating one or more lights or outputting sound or a tone) or instructions (e.g., verbal instructions) to guide a feeder (such as a parent, a doula, a baby sitter, etc.) to regulate a number of sucks per burst, a respiratory rate and/or a duration of bursts and pauses (or pacing) by adjusting a flow rate dial and/or an angle of the bottle. For example, the feedback may include selective illumination of a green, yellow or red light emitting diode (LED) to indicate the quality of the feeding.

In some embodiments, monitoring device 110, electronic device 112 and/or computer system 130 may compute diagnostic information associated with feeding/oromotor difficulties based at least in part on the one or more oral-motor metrics, the one or more feeding quality metrics and/or analysis of the measurements. This diagnostic information may be provided or presented by monitoring device 110 and/or electronic device 112. For example, electronic device 112 may display information corresponding to the diagnostic information in the user interface.

Note that the diagnostic information may include: a feeding performance score. Moreover, the diagnostic information may include or may correspond to: possible developmental delays, the possible tongue-tie, the possible excessive air swallowing into the stomach and/or possible feeding difficulties. Notably, the diagnostic information may include one or more risk scores for the possible developmental delays, the possible tongue-tie, and/or the possible feeding difficulties. In some embodiments, the possible feeding difficulties may include: reflux, colic, and/or a type of oral-motor functional impairment.

Furthermore, monitoring device 110, electronic device 112 and/or computer system 130 may compute one or more feeding quality metrics based at least in part on the one or more oral-motor metrics and/or analysis of the measurements, where the one or more feeding quality metrics may include: oral pressure, feeding consistency, and/or a sucking/swallowing/breath rate. Additionally, the monitoring device may compute a normalized maturity index of the baby based at least in part on the one or more oral-motor metrics, the one or more feeding quality metrics and/or analysis of the measurements, which include indices of disordered feeding. In some embodiments, the normalized maturity index corresponds to a ratio of a developmental metrics of the baby and a chronological age of the baby. Note that the normalized maturity index may correspond to a neurological development of the baby.

In some embodiments, analysis results, diagnostic information, feedback, and/or the one or more feeding quality metrics may be aggregated over time, e.g., by computer system 130, into a history over a time interval or a summary report. This aggregated information may be reported to a user of monitoring device 110 and/or electronic device 112, e.g., a parent. Alternatively or additionally, the history or summary report may, with user approval/authorization, be provided to a feeding consultant or a medical professional. For example, computer system 130 may provide the history or summary report to computer 132, which is associated with the feeding consultant or the medical professional. The feeding consultant or the medical professional may use this information to: provide further guidance regarding feeding; diagnose one or more medical conditions (such as autism); and/or prescribe or recommend additional treatment(s) or intervention(s). Note that the history or summary report may be used in a clinical trial or in analysis of a population of babies.

Note that the analysis of the measurements to calculate the analysis results, the computing of the diagnostic information, the determining of the feedback, and/or the computing of the one or more feeding quality metrics may be performed in a variety of ways. For example, one or more of the aforementioned operations may involve statistical calculations and/or comparisons with baseline information for a baby and/or a population of babies (such as historical values stored by computer system 130). As described further below with reference to FIGS. 22-24, in some embodiments the analysis of the measurements includes VMD.

Alternatively or additionally, the analysis of the measurements to calculate the analysis results, the computing of the diagnostic information, the determining of the feedback, and/or the computing of the one or more feeding quality metrics may be performed using an analysis model that is pretrained or predetermined using a machine-learning technique (such as a supervised learning technique, an unsupervised learning technique and/or a neural network) and a training dataset. For example, the analysis model may include a classifier or a regression model that was trained using: a support vector machine technique, a classification and regression tree technique, logistic regression, LASSO, linear regression, a neural network technique (such as a convolutional neural network technique, a long short-term memory or LSTM neural network technique, an autoencoder neural network or another type of neural network technique) and/or another linear or nonlinear supervised-learning technique. The analysis model may use measurements, analysis results and/or one or more feeding quality metrics as inputs and may output: the analysis results, the diagnostic information, the feedback (such as a recommendation for an improved feeding technique), and/or one or more feeding quality metrics. Note that computer system 130 may dynamically retrain the analysis model based at least in part on updates to the training dataset (such as recent measurements, analysis results and/or one or more feeding quality metrics associated with one or more babies), and then may provide an updated analysis model to: monitoring device 110 and/or electronic device 112. As discussed further below, FIGS. 25 and 26 illustrate a neural network and associated receiver operator characteristics.

In these ways, the monitoring techniques may facilitate real-time (during feeding) and real-world monitoring of feeding, and may provide real-time and real-world feedback on how to improve the feeding. Moreover, by using one or more non-invasive sensors, the monitoring techniques may not disrupt the feeding process. Furthermore, the monitoring techniques may provide diagnostic information and additional information that allows: medical conditions to be diagnosed, current therapies and interventions to be assessed, and/or additional therapies and interventions to be identified. These capabilities may assist parents and feeding consultants and medical professionals, and may improve the health and well-being of babies.

While the preceding embodiments illustrated the use of the monitoring techniques in conjunction with bottle feeding, in other embodiments the monitoring techniques may be used with breastfeeding. For example, the monitoring device may be adapted to be positioned over the areola of the breast. When a baby sucks on a nipple included in the monitoring device, corresponding mechanical suction or motion may be applied to the breast nipple to stimulate milk flow. Then, the monitoring device may be used to assess the feeding while the baby is breastfeeding.

Figure 2:
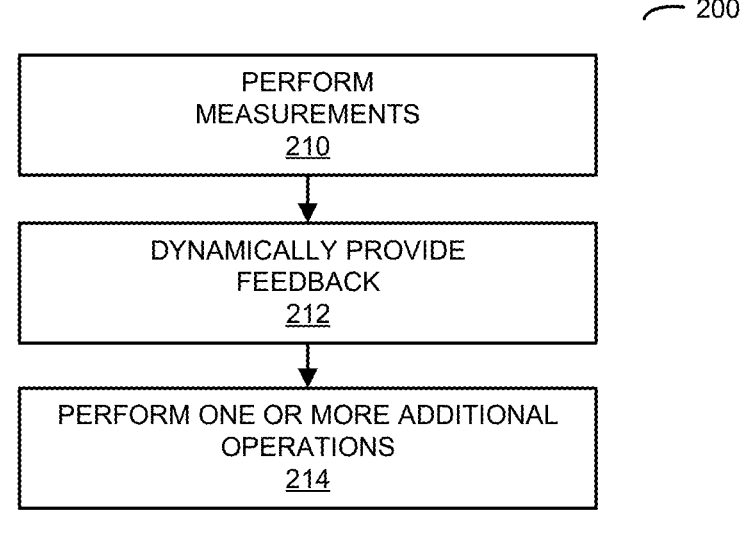
FIG. 2 is a flow diagram illustrating an example of a method for providing feedback using a monitoring device in FIG. 1 in accordance with an embodiment of the present disclosure.

We now describe embodiments of the method. FIG. 2 presents a flow diagram illustrating an example of a method 200 for providing feedback in accordance with an embodiment of the present disclosure, which may be performed by a monitoring device (such as monitoring device 110 in FIG. 1). During operation, the monitoring device may perform measurements (operation 210) while a baby is performing the feeding, where the measurements are associated with sucking, swallowing and breathing by the baby. Then, the monitoring device may dynamically provide the feedback (operation 212) based at least in part on the measurements, where the feedback includes: when to dynamically pause the feeding, a change to a flow rate during the feeding, a change to a size of the nipple, a change to a size of the baby bottle, a change to promote stronger sucking by the baby, a change to an anatomical position of the baby during the feeding, a recommendation for a swallowing study, a recommendation for the baby to use a pacifier between instances of the feeding, diagnostic information about a possible (such as presence of or a risk of) tongue-tie, diagnostic information about possible excessive air swallowing into the stomach and/or a recommendation for additional therapy for the baby.

For example, the feedback may include: signals or instructions to guide a feeder to regulate a number of sucks per burst (or sequence of swallows), a respiratory rate and/or a duration of bursts and pauses or time intervals between swallows by adjusting a flow rate dial and/or an angle of the baby bottle.

Note that the feedback may be based at least in part on a modal decomposition of the measurements (such as VMD of the measurements) and/or a pretrained analysis model (such as a neural network).

Moreover, the feedback may include information a quality of the feeding while the baby is feeding.

Furthermore, the measurements may be non-invasive and may be performed without the sensors being placed in a mouth of the baby.

Note that the set of sensors may include two or more sensors. For example, the set of sensors may include: a pressure sensor, an acoustic sensor, an accelerometer, a LiDAR sensor and/or an infrared sensor.

Additionally, the measurements may correspond to one or more oral-motor metrics associated with the baby. For example, the one or more oral-motor metrics may include: tongue kinetics, a force of sucking, a suction and expression pressure, the flow rate, a sucking/swallowing/breathe ratio, micro-gagging, a pressure of lip seal, a pressure of tongue, and/or distance from monitoring device to a top of a fluid level line in the baby bottle.

In some embodiments, the monitoring device may optionally perform one or more additional operations (operation 214). For example, the monitoring device may provide, addressed to an electronic device (which is separate from the monitoring device), information associated with the measurements. Next, the monitoring device may receive the feedback associated with the electronic device.

Moreover, the monitoring device may analyze the measurements and/or may determine the feedback. In some embodiments, the analysis may include computing the one or more oral-motor metrics based at least in part on the measurements. Alternatively or additionally, the feedback may include the one or more oral-motor metrics. For example, the monitoring device may provide diagnostic information associated with feeding/oromotor difficulties based at least in part on the analysis of the measurements and/or the one or more oral-motor metrics. Note that the diagnostic information may include: a feeding performance score or a risk score. Furthermore, the diagnostic information may include or may correspond to: possible developmental delays, the possible tongue-tie, and/or possible feeding difficulties. In some embodiments, the possible feeding difficulties may include: reflux, colic, the excessive air swallowing into the stomach and/or a type of oral-motor functional impairment.

Additionally, the monitoring device may compute and/or the feedback may include one or more feeding quality metrics based at least in part on the analysis and/or the one or more oral-motor metrics, where the one or more feeding quality metrics may include: oral pressure, feeding consistency (e.g., on a 0-10 scale), and/or a sucking/swallowing/breath rate. In some embodiments, the monitoring device may compute and/or the feedback may include a normalized maturity index of the baby (which may provide an intelligence quotient for oral-motor skills) based at least in part on the analysis, the one or more oral-motor metrics and/or the one or more feeding quality metrics, which may include indices of disordered feeding. Note that the normalized maturity index corresponds to a ratio of a developmental metrics of the baby and a chronological age of the baby.

Thus, in some embodiments, the monitoring device may compute the one or more oral-motor metrics, feeding quality (such as the one or more feeding quality metrics), the feedback and/or the diagnostic information based at least in part on the measurements. Alternatively or additionally, in some embodiments, the monitoring device may provide the measurements to an electronic device, and may receive information specifying the one or more oral-motor metrics, the feeding quality, the feedback and/or the diagnostic information.

Figure 3:
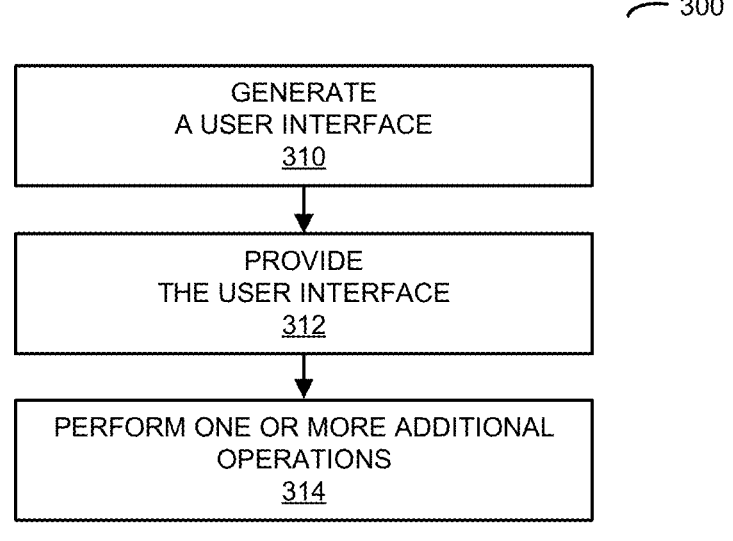
FIG. 3 is a flow diagram illustrating an example of a method for providing feedback using an electronic device in FIG. 1 in accordance with an embodiment of the present disclosure.

FIG. 3 presents a flow diagram illustrating an example of a method 300 for providing feedback in accordance with an embodiment of the present disclosure, which may be performed by an electronic device (such as electronic device 112 in FIG. 1). During operation, the electronic device may generate a user interface (operation 310). Then, the electronic device may display, on a display, the user interface (operation 312). This user interface may include information that specifies dynamic feedback associated with feeding by a baby using a baby bottle, where the feedback is based at least in part on analysis of measurements performed while the baby is performing the feeding.

Note that the feedback may include: when to dynamically pause the feeding, a change to a flow rate during the feeding, a change to a size of the nipple used during the feeding, a change to a size of the baby bottle during the feeding, a change to promote stronger sucking by the baby, a change to an anatomical position of the baby during the feeding, a recommendation for a swallowing study, a recommendation for the baby to use a pacifier between instances of the feeding, diagnostic information about a possible tongue-tie, diagnostic information about possible excessive air swallowing into the stomach and/or a recommendation for additional therapy for the baby.

Moreover, the feedback may be based at least in part on a modal decomposition of the measurements (such as VMD of the measurements) and/or a pretrained analysis model (such as a neural network).

Furthermore, the feedback may include information a quality of the feeding while the baby is feeding. Note that the feedback may be provided while the baby is performing the feeding.

Additionally, the measurements may correspond to the one or more oral-motor metrics associated with the baby. For example, the one or more oral-motor metrics may include: tongue kinetics, a force of sucking, a suction and expression pressure, a flow rate, a sucking/swallowing/breathe ratio, micro-gagging, a pressure of lip seal, a pressure of tongue, and/or distance from a monitoring device (which may be mechanically coupled to a bottle and a nipple) to a top of a fluid level line in the baby bottle.

Note that the user interface may include one or more graphs of the feedback as a function of time or tables of data, analysis results and/or the one or more oral-motor metrics.

In some embodiments, the electronic device may optionally perform one or more additional operations (operation 314). For example, the electronic device may receive, associated with the monitoring device (which is separate from the electronic device), information associated with the measurements and/or one or more oral-motor metrics associated with the baby and corresponding to the measurements. Next, the electronic device may analyze the measurements and/or may determine the feedback.

In some embodiments, the analysis may include computing the one or more oral-motor metrics based at least in part on the measurements. Alternatively or additionally, the feedback may include the one or more oral-motor metrics. For example, the electronic device may provide diagnostic information associated with feeding/oromotor difficulties based at least in part on the analysis of the measurements and/or the one or more oral-motor metrics. Note that the diagnostic information may include: a feeding performance score or a risk score. Furthermore, the diagnostic information may include or may correspond to: possible developmental delays, the possible tongue-tie, and/or possible feeding difficulties. In some embodiments, the possible feeding difficulties may include: reflux, colic, the excessive air swallowing into the stomach and/or a type of oral-motor functional impairment.

Additionally, the electronic device may compute and/or the feedback may include one or more feeding quality metrics based at least in part on the analysis and/or the one or more oral-motor metrics, where the one or more feeding quality metrics may include: oral pressure, feeding consistency, and/or a sucking/swallowing/breath rate. In some embodiments, the electronic device may compute and/or the feedback may include a normalized maturity index based at least in part on the analysis, the one or more oral-motor metrics and/or the one or more feeding quality metrics, which may include indices of disordered feeding. Note that the normalized maturity index corresponds to a ratio of a developmental metrics of the baby and a chronological age of the baby.

Alternatively or additionally, the electronic device may receive, associated with a computer system (which is separate from the electronic device) the feedback.

Moreover, the electronic device may provide at least some of the feedback to the monitoring device. For example, at least some of the feedback provided to the monitoring device may correspond to or may include: signals or instructions to guide a feeder to regulate a number of sucks per burst (or sequence of swallows), a respiratory rate and/or a duration of bursts and pauses or time intervals between swallows by adjusting a flow rate dial and/or an angle of the baby bottle.

Thus, in some embodiments, the electronic device may compute the one or more oral-motor metrics, feeding quality (such as the one or more feeding quality metrics), the feedback and/or the diagnostic information based at least in part on the measurements. Alternatively or additionally, in some embodiments, the electronic device may receive (e.g., associated with the computer system) information specifying the one or more oral-motor metrics, the feeding quality, the feedback and/or the diagnostic information.

In some embodiments of method 200 (FIG. 2) and/or 300, there may be additional or fewer operations. Furthermore, the order of the operations may be changed, and/or two or more operations may be combined into a single operation.

Figure 4:
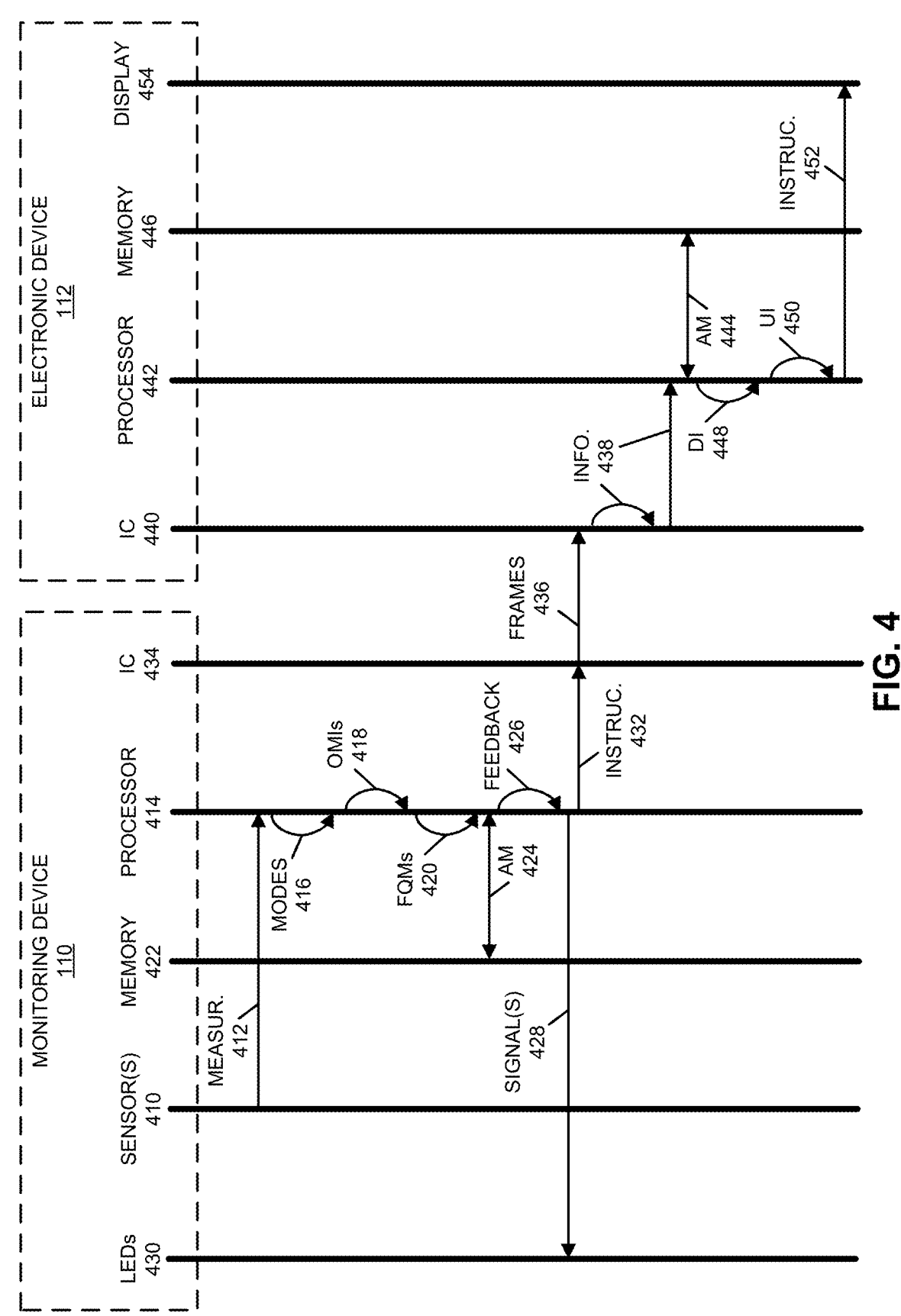
FIG. 4 is a drawing illustrating an example of communication between a monitoring device and an electronic device in FIG. 1 in accordance with an embodiment of the present disclosure.

Embodiments of the monitoring techniques are further illustrated in FIG. 4, which presents a drawing illustrating an example of communication among components in monitoring device 110 and electronic device 112 in accordance with an embodiment of the present disclosure. In FIG. 4, one or more sensors 410 in monitoring device 110 may perform measurements 412 (such as non-invasive measurements) while a baby is feeding. These measurements may be provided to a processor 414 in monitoring device 110.

Then, processor 414 may analyze measurements 412 to determine modes 416. In some embodiments, processor 414 may analyze measurements 412 to optionally calculate one or more oral-motor metrics (OMIs) 418. Moreover, processor 414 may optionally compute one or more feeding quality metrics (FQMs) 420 based at least in part on measurements 412 and/or the OMIs 418.

Furthermore, processor 414 may determine feedback 426 about feeding quality based at least in part on modes 416, the one or more oral-motor metrics 418 and/or one or more feeding quality metrics 420. Note that determining feedback 426 may involve processor 414 accessing a pretrained analysis model (AM) 424 in memory 422 in monitoring device 110. This analysis model may use modes 416, the one or more oral-motor metrics 418 and/or the one or more feeding quality metrics 420 as inputs and may output feedback 426. Next, processor 414 may dynamically provide one or more signals 428 to one or more LEDs 430 in monitoring device 110 in order to provide feedback 426 about the feeding. For example, the one or more signals 428 may illuminate: a green LED when the feeding quality is good, a yellow LED when the feeding quality is ok, and a red LED when the feeding quality is poor.

Additionally, processor 414 may provide an instruction 432 to interface circuit (IC) 434 in monitoring device 110. In response, interface circuit 434 may provide one or more packets or frames 436 to electronic device 112 with information 438 specifying or corresponding to: measurements 412, modes 416, one or more oral-motor metrics 418, one or more feeding quality metrics 420, and/or feedback 426.

After receiving the one or more packets or frames 436, an interface circuit 440 in electronic device 112 may provide information 438 to processor 442 in electronic device 112. Then, processor 442 may determine diagnostic information (DI) 448 based at least in part on: measurements 412, modes 416, one or more oral-motor metrics 418, one or more feeding quality metrics 420, and/or feedback 426. For example, processor 442 may accessing a pretrained analysis model 444 in memory 446 in electronic device 112. This analysis model may use modes 416, the one or more oral-motor metrics 418, the one or more feeding quality metrics 420 and/or feedback 422 as inputs and may output diagnostic information 448.

Next, processor 442 may generate a user interface (UI) 450 based at least in part on modes 416, the one or more oral-motor metrics 418, the one or more feeding quality metrics 420, feedback 426 and/or diagnostic information 448. Moreover, processor 442 may provide instructions 452 to a display 454 in electronic device 112 to display user interface 450.

While FIG. 4 illustrates communication between components using unidirectional or bidirectional communication with lines having single arrows or double arrows, in general the communication in a given operation in this figure may involve unidirectional or bidirectional communication.

We now further describe embodiments of the monitoring techniques. Notably, the monitoring device may be a sensorized, infant baby-bottle collar that is designed to detect sucking, breathing, swallowing, and/or fluid consumption during a feeding session. The monitoring device may: acquire sensor data from the bottle collar, compute salient features of such data, and/or communicate the data and/or the features via Bluetooth to a cellular telephone.

A mobile application, installed on and that executes in an environment (or operating system) of the cellular telephone, may analyze the data and/or the features to assess an infant's oral-motor skills. For example, a set of feeding performance metrics may be calculated by the application and may be provided along with other pertinent information (which is sometimes generally referred to as 'feedback') to parents and/or their clinicians to help support the infant's developmental skill progression.

By detecting patterns in the data and/or the features, the monitoring device may be able to assess variations of typical feeding (e.g., satiety, reflux, colic, etc.) and may help guide parents and/or clinicians to improved or optimal feeding strategies. The bottle collar may also be able to instruct parents on improved or optimal angles for pacing and, thus, a feeding strategy that enables a baby to better control milk flow as in breastfeeding. In some embodiments, the monitoring device may recognize atypical patterns of neuromotor dysfunction (such as sensorimotor delays that may indicate risk for speech or other neurodevelopmental disorders), thereby allowing timely connection with specialists for proper diagnosis and treatment.

Furthermore, because oral-motor skills are important in feeding and language development, the monitoring techniques may help identify atypical skills while supporting appropriate early interventions. Access to speech/feeding therapists who are able to identify lagging skills and provide support is often limited. Indeed, there are no currently available objective tools that assess the feeding skills outside of a hospital or a clinical setting. In contrast, the monitoring device to assess feeding following hospital discharge for infants who are, e.g., from term age through the first year. It can also be used with a variety of different mouth pieces to help guide maturation. Additionally, the monitoring device may include capabilities beyond sucking pressure measurement and may not require direct contact with the infant's oral cavity. As noted previously, integrating various sensors into a purpose-built bottle collar may assist in identification of atypical patterns of development.

For example, a baby with autism may have normal feeding quality metrics for the first 5-6 months. While the baby may still appear normal from 6-12 months of age, there is typically a falloff in oral-motor metrics that indicates sensor-motor dysfunction, which may be detected using the monitoring techniques. Alternatively, the monitoring techniques may detect tongue-ties, which may not be visible, but which may result in a functional impairment (and which can lead to language or feeding problems). Furthermore, the monitoring techniques may provide objective information regarding reflex, which can be associated with an immature gastrointestinal track. Notably, if a pediatrician unnecessarily prescribes antacids, a baby may become more susceptible to allergies or infections. In order to prevent this, the monitoring techniques may allow disorganized or dysfunctional feeding to be determined, which can help the pediatrician determine the appropriate therapy or intervention.

Note that a standalone plastic collar or, in some embodiments, a nipple/collar combination may be designed for parents to use with existing baby bottles (including wide neck and standard neck bottles) and ensures that there is no possible contamination of milk or electrical contact between the baby and the internal electronics. In some embodiments, the monitoring device may be cleaned using soap and water.

The monitoring device may include multiple electronic sensors that support the measurement of: intraoral sucking pressure, expression pressure, breathing, swallowing, fluid consumption volume, physical bottle orientation, and/or motion during infant feeding sessions. Data acquisition from the sensors may be controlled by a microcontroller platform that includes: a processor, onboard memory to store raw sensor readings, and/or firmware and analysis techniques that compute feeding metrics and other salient feeding parameters. Moreover, the bottle collar electronics may include Bluetooth services and data payloads programmed into firmware that support broadcasting or interrogation of acquired sensor data and computed feeding-performance metrics by external Bluetooth-compatible electronic devices, such as smartphones running the companion application.

In some embodiments, the analysis performed by the monitoring device and/or the application on the electronic device may include signal processing and other analysis techniques. For example, at least some of the analysis may be performed using a pretrained analysis model (such as a machine-learning technique) to produce a feeding-skill maturity index with respect to age-matched norms. Moreover, pattern-recognition techniques may generate support guidance or feedback for parents via the application on the electronic device. Furthermore, via the application on the electronic device, parents can identify lagging feeding-skill areas, including dysfunctional and disorganized feeding skills. Additionally, feeding tips may be provided based at least in part on individual or infant-specific metrics. Note that a cloud-based computer system may communicate with the monitoring device and/or the application on the electronic device, which may allow parents and/or clinicians to track oral-motor skill progress over time, including over the first year of infant life.

Figure 5:
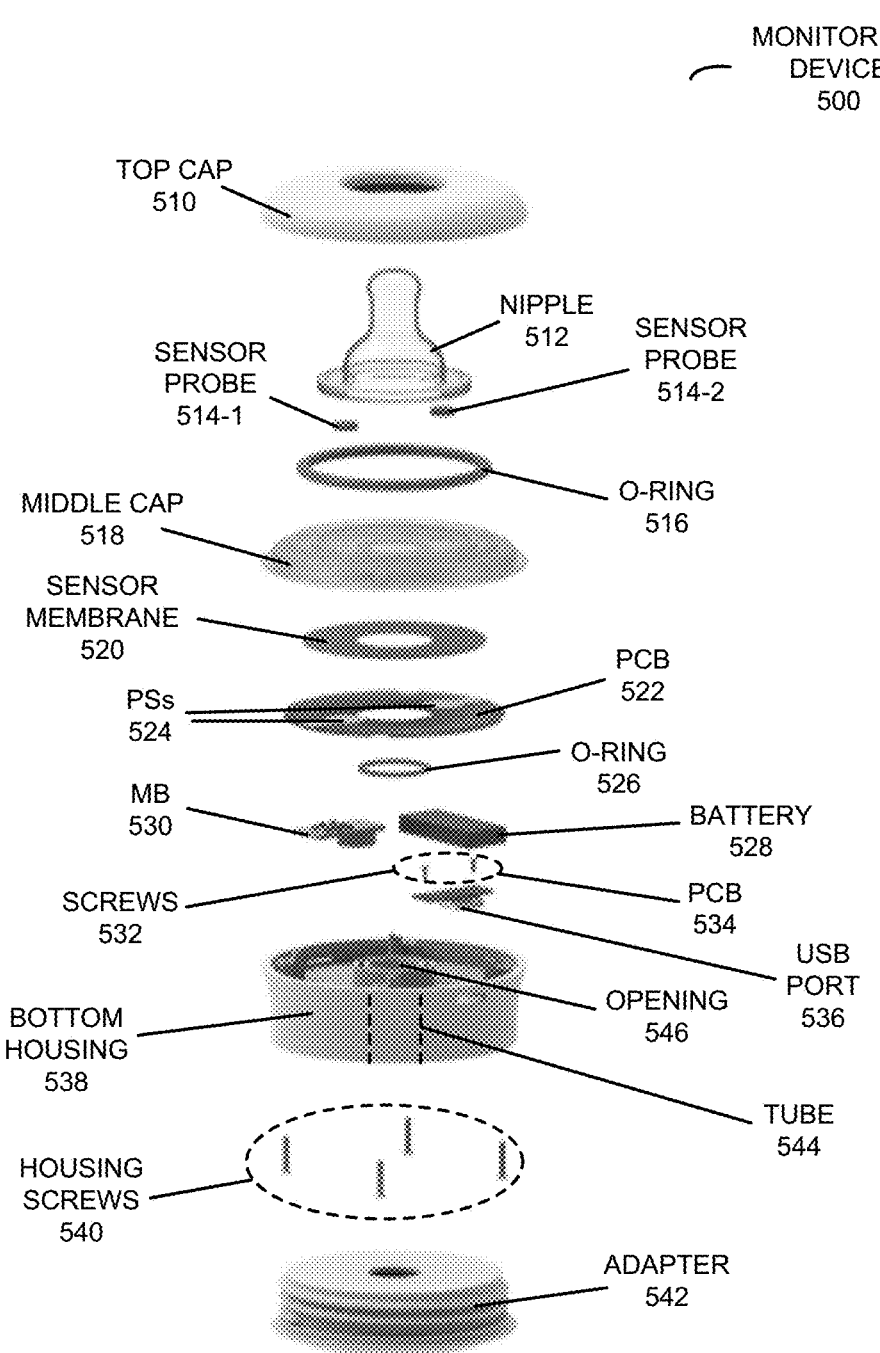
FIG. 5 is a drawing illustrating an example of an exploded view of a monitoring device in accordance with an embodiment of the present disclosure.

FIG. 5 presents a drawing illustrating an example of an exploded view of a monitoring device 500 in accordance with an embodiment of the present disclosure. This monitoring device includes: a top cap 510, a silicone nipple 512, silicone sensor probes 514, a silicone O-ring 516, a middle cap 518, a silicone sensor membrane 520, a printed circuit board (PCB) 522 with one or more pressure sensors (PSs) 524, a silicone O-ring 526, a battery 528, a microphone board (MB) 530, screws 532, a printed circuit board 534, a universal serial bus (USB) port 536, a bottom housing 538 (which is sometimes referred to as a 'housing'), housing screws 540, and/or an optional narrow bottle-cap adapter 542. Note that bottom housing 538 and/or optional adapter 542 (for a baby bottle with a narrow neck) may mechanically couple to a baby bottle and either of their threads (which are shown in FIG. 7) are sometimes referred to as a 'first connector.' Moreover, top cap 510, which mechanically secures nipple 512 to monitoring device 500, is sometimes referred to as a 'second connector.' Furthermore, bottom housing 538 may include an internal tube 544 (indicated by the dashed lines on bottom housing 538) having a first opening (which is not visible in FIG. 5) defined by a first edge proximate to or on the same side of bottom housing 538 the first connector, and a having second opening 546 defined by a second edge proximate to or on the same side of bottom housing 538 as the second connector.

Figure 6:
FIG. 6 is a drawing illustrating an example of an assembled monitoring device in accordance with an embodiment of the present disclosure.

FIG. 6 presents a drawing illustrating an example of an assembled monitoring device 500 in accordance with an embodiment of the present disclosure.

Figure 7:
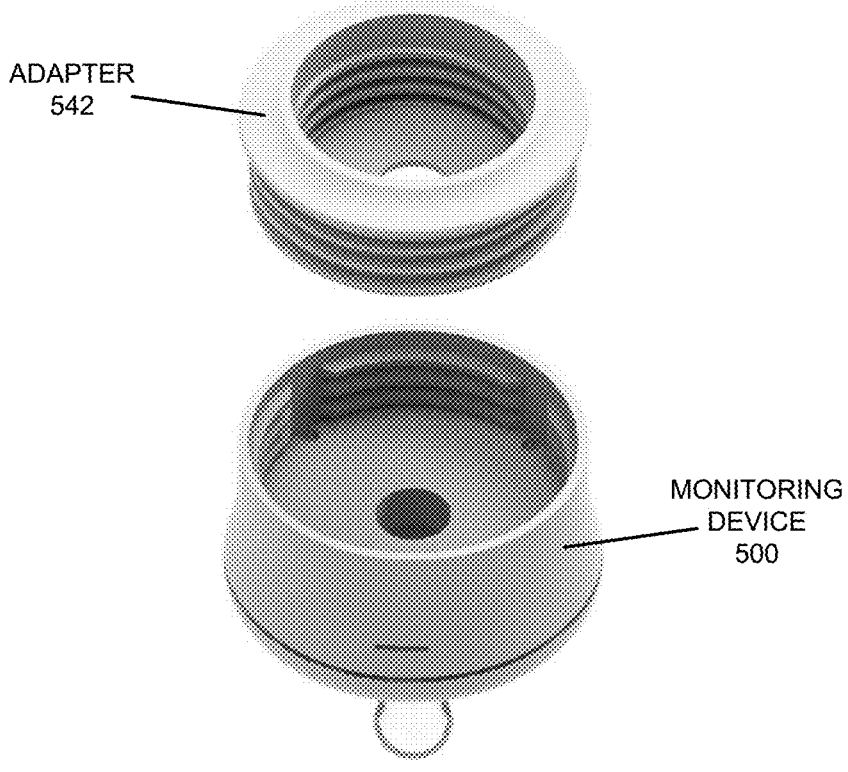
FIG. 7 is a drawing illustrating an example of a monitoring device and an optional adaptor in accordance with an embodiment of the present disclosure.
Figure 8:
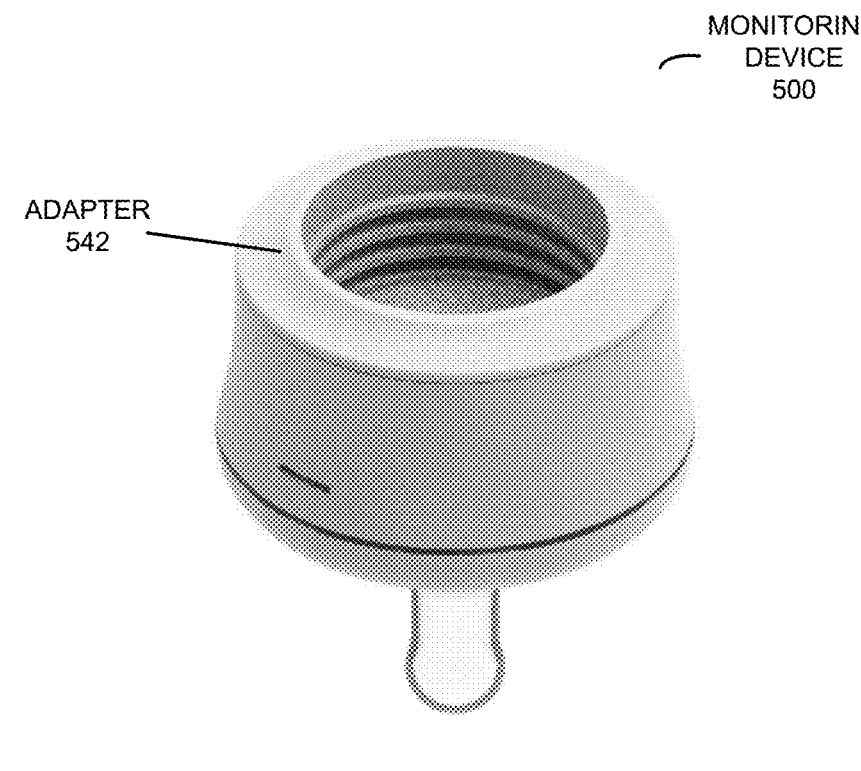
FIG. 8 is a drawing illustrating an example of a bottom view of monitoring device with an optional adaptor screwed into place in accordance with an embodiment of the present disclosure.

Moreover, FIG. 7 presents a drawing illustrating an example of a monitoring device 500 and an optional adaptor 542 for a baby bottle with a narrow neck in accordance with an embodiment of the present disclosure. Furthermore, FIG. 8 presents a drawing illustrating an example of a bottom view of monitoring device 500 with optional adaptor 542 screwed into place in accordance with an embodiment of the present disclosure.

Figure 9:
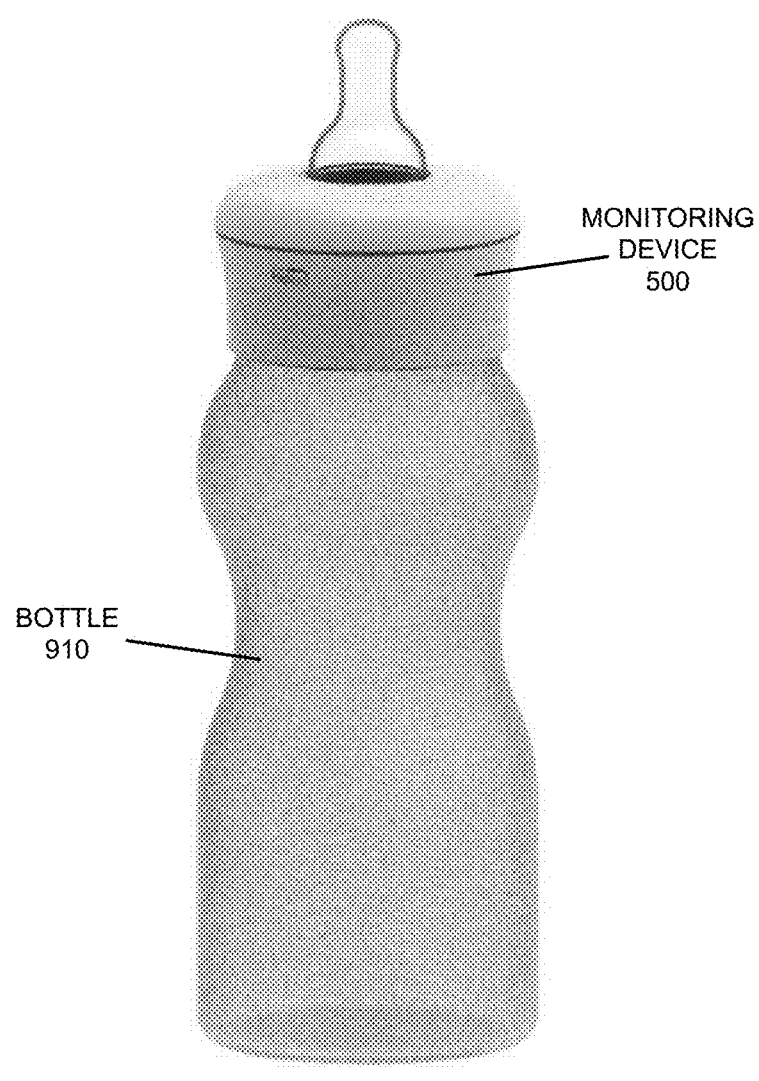
FIG. 9 is a drawing illustrating an example of a monitoring device mechanically coupled to a bottle in accordance with an embodiment of the present disclosure.

FIG. 9 presents a drawing illustrating an example of a monitoring device 500 mechanically coupled to a bottle 910 in accordance with an embodiment of the present disclosure.

Figure 10:
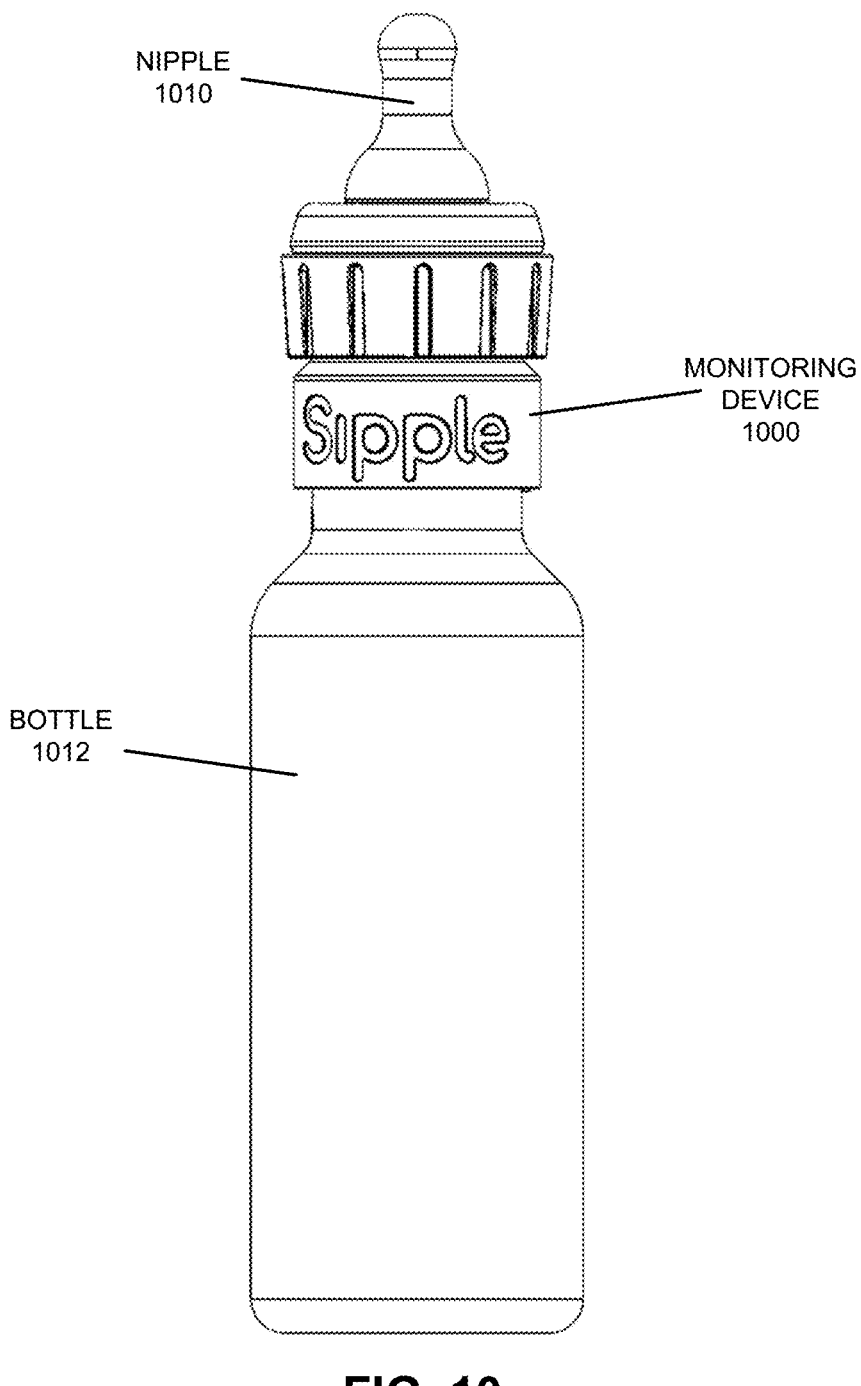
FIG. 10 is a drawing illustrating an example of an assembled monitoring device, a nipple and a bottle in accordance with an embodiment of the present disclosure.

FIG. 10 presents a drawing illustrating an example of an assembled monitoring device 1000, a nipple 1010 and a bottle 1012 in accordance with an embodiment of the present disclosure. Moreover, FIG. 11 presents a drawing illustrating an example of a cross-sectional view of an assembled monitoring device 1100, a nipple 1110 and a bottle 1112 in accordance with an embodiment of the present disclosure.

Figure 11:
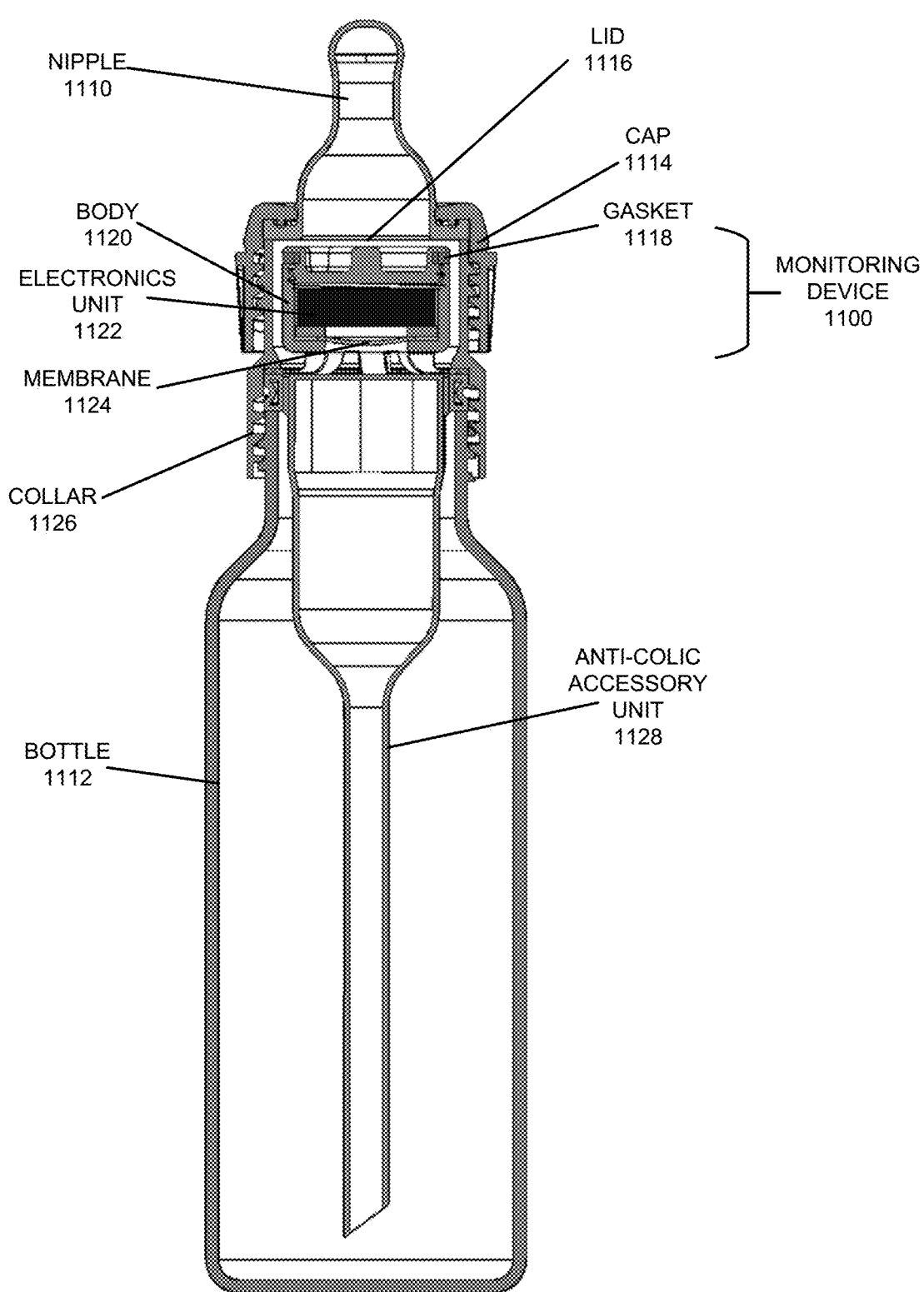
FIG. 11 is a drawing illustrating an example of a cross-sectional view of an assembled monitoring device, a nipple and a bottle in accordance with an embodiment of the present disclosure.

In FIG. 11, cap 1114 may mechanically couple monitoring device 1100 and nipple 1110. Moreover, monitoring device 1100 may include: a lid 1116, an O-ring gasket 1118, a body 1120, an electronics unit 1122, a transparent silicone membrane 1124 (which may allow pressure changes from outside of electronics unit 1122 to be measured and which may seal electronics unit 1122 from fluid in bottle 1112), and a collar 1126 to mechanically couple monitoring device 1100 to bottle 1112. Note that electronics unit 1122 may include: a barometric pressure sensor, a time-of-flight sensor, an accelerometer (or IMU), a microphone (such as an omnidirectional microphone), a Bluetooth low energy module, and a battery. In some embodiments, there may be an optional anti-colic accessory 1128.

Figure 12:
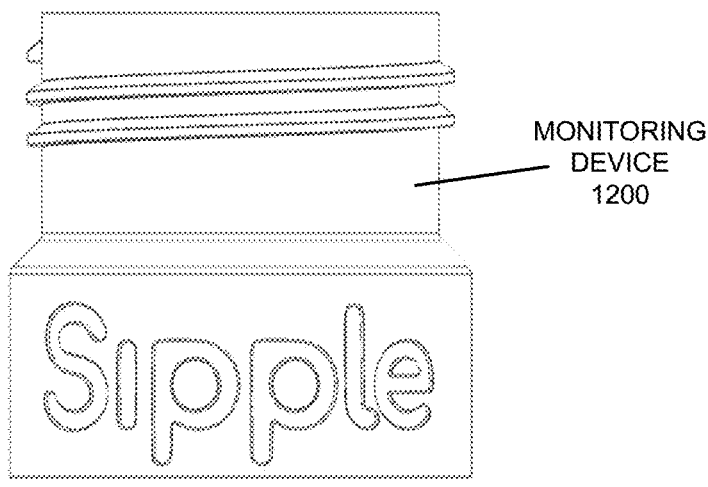
FIG. 12 is a drawing illustrating an example of an assembled monitoring device in accordance with an embodiment of the present disclosure.
Figure 13:
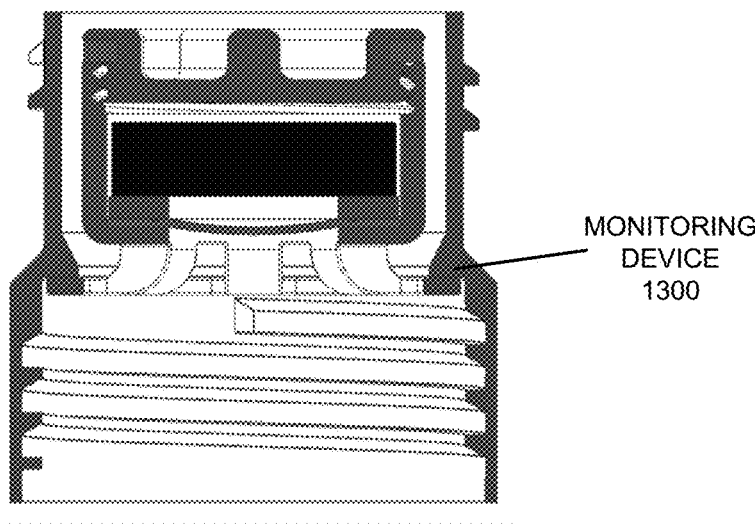
FIG. 13 is a drawing illustrating an example of a cross-sectional view of an assembled monitoring device in accordance with an embodiment of the present disclosure.

FIG. 12 presents a drawing illustrating an example of an assembled monitoring device 1200 in accordance with an embodiment of the present disclosure. Moreover, FIG. 13 presents a drawing illustrating an example of a cross-sectional view of an assembled monitoring device 1300 in accordance with an embodiment of the present disclosure. Furthermore, FIG. 14 presents a drawing illustrating an example of an exploded view of an assembled monitoring device 1400 in accordance with an embodiment of the present disclosure.

Figure 14:
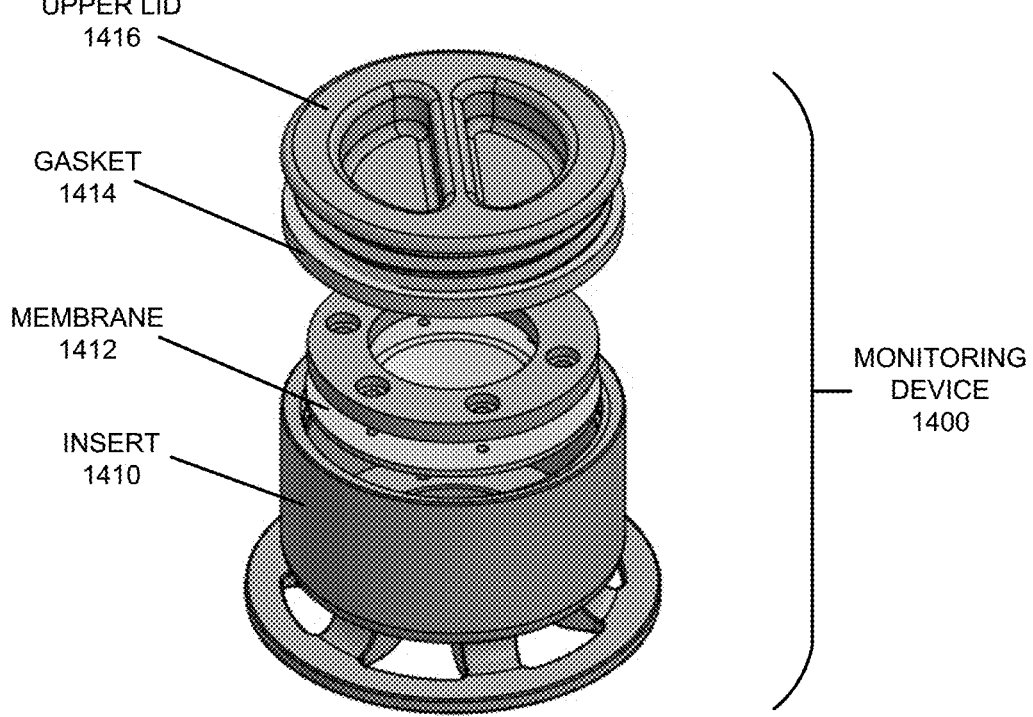
FIG. 14 is a drawing illustrating an example of an exploded view of an assembled monitoring device in accordance with an embodiment of the present disclosure.
Figure 15:
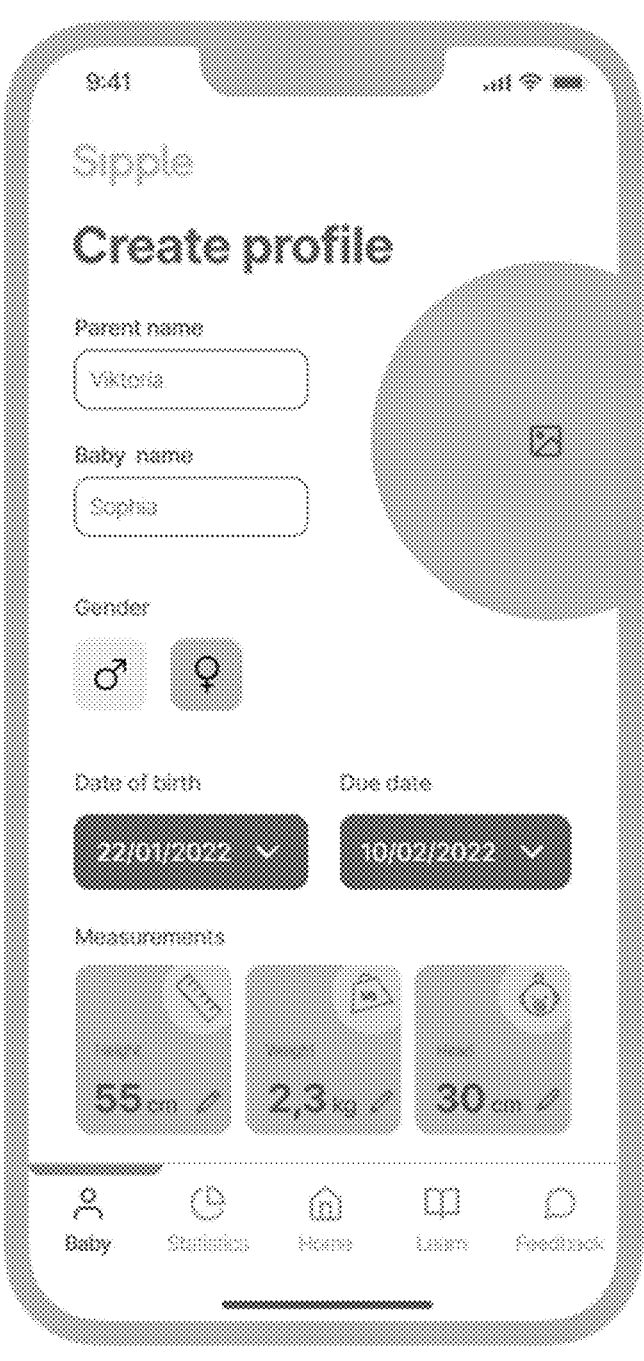
FIGS. 15-21 are drawings illustrating examples of user interfaces associated with an application executing on an electronic device in accordance with an embodiment of the present disclosure.
Figure 16:
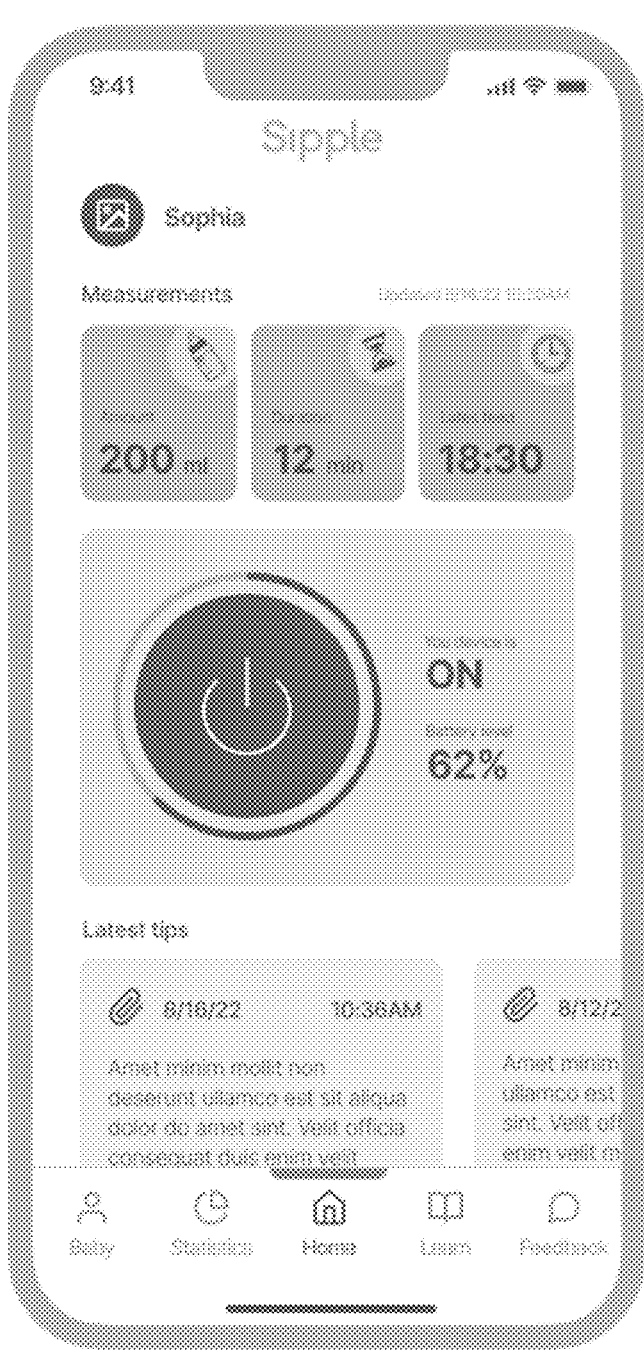
Figure 17:
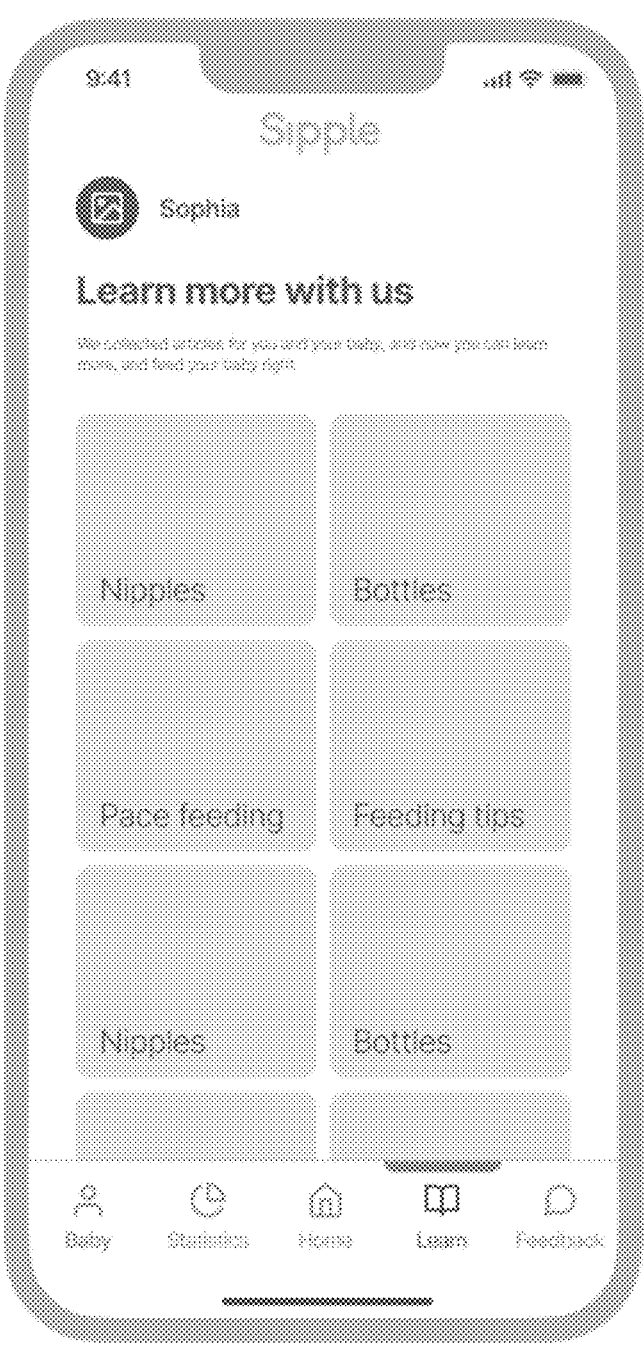
Figure 18:
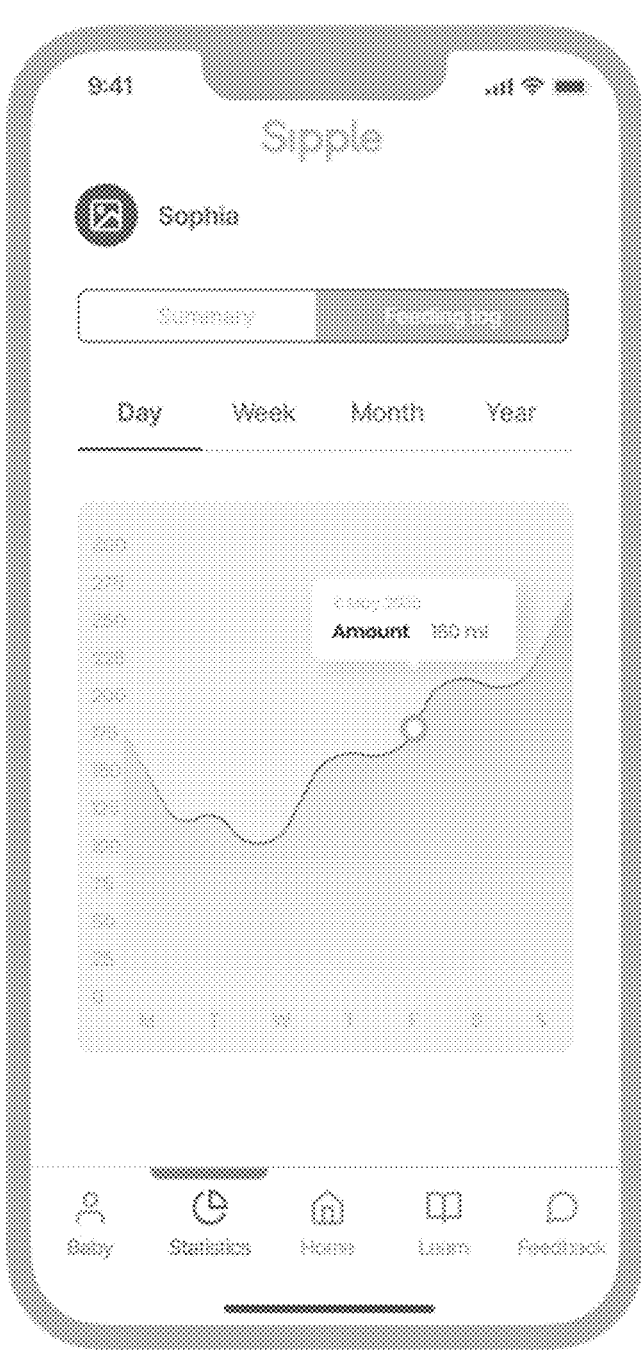
Figure 19:
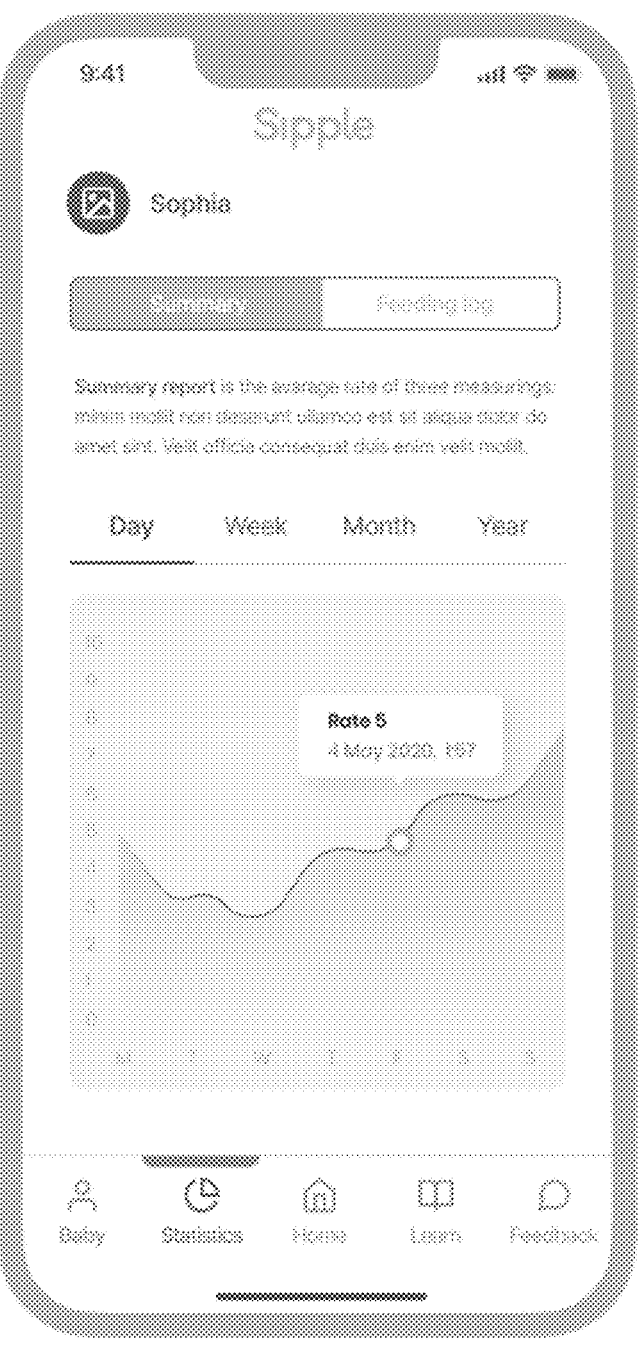
Figure 20:
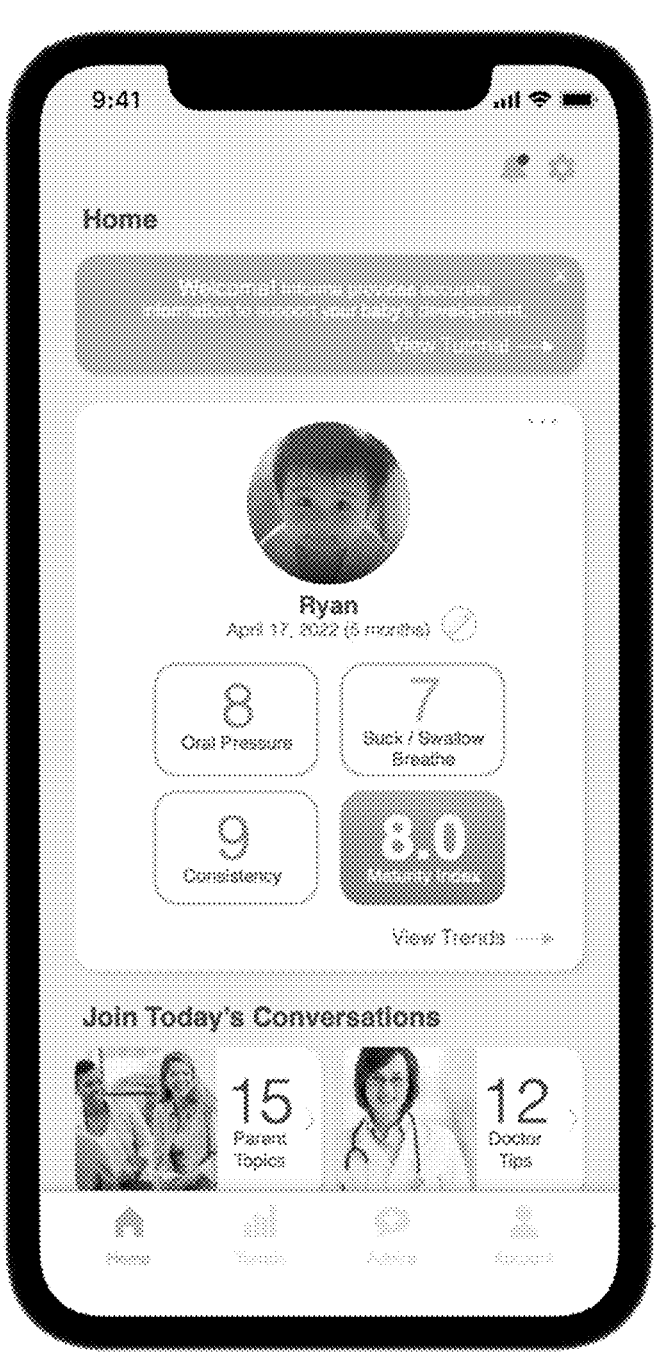
Figure 21:
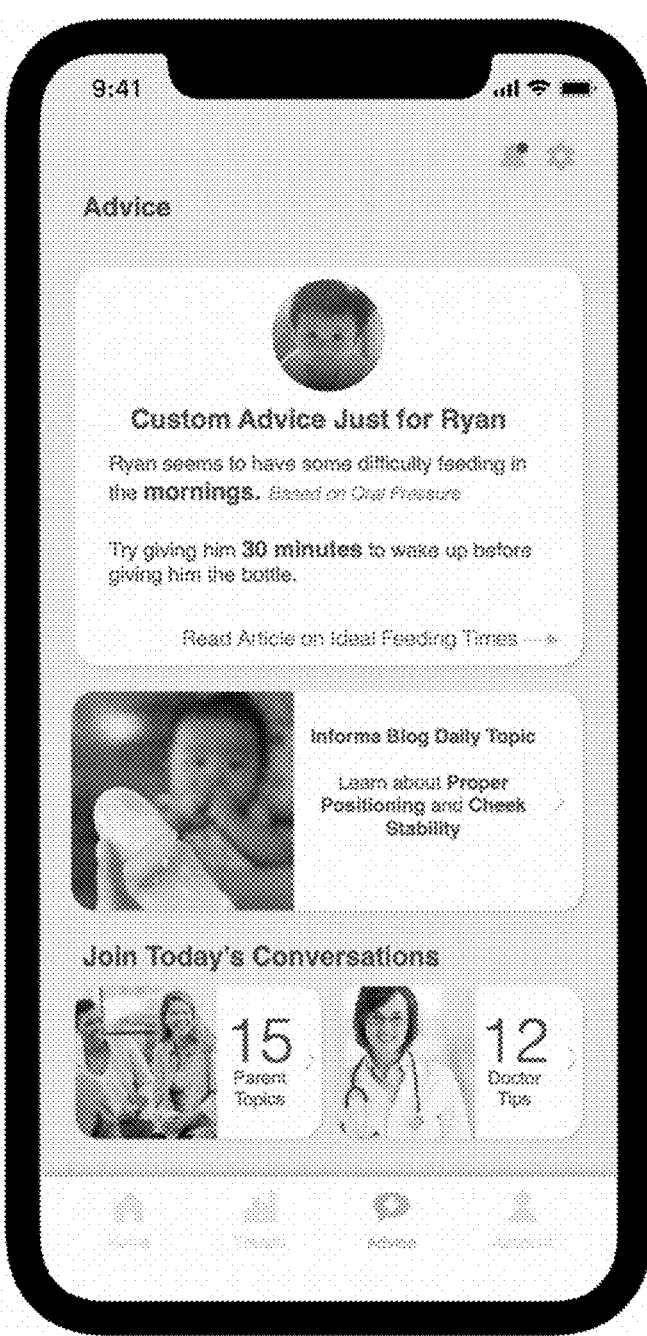

In FIG. 14, monitoring device 1400 may include: an insert 1410, a membrane 1412, a gasket 1414 and an upper lid 1416.

FIGS. 15-21 present drawings illustrating examples of user interfaces associated with an application executing on an electronic device (such as electronic device 112 in FIG. 1) in accordance with an embodiment of the present disclosure. These user interfaces may be used to receive and present information, such as feedback about feeding.

We now further describe embodiments of the analysis of the measurements, the pretrained analysis model and the feedback in the monitoring techniques. In some embodiments, the measurements may include an acoustic signal corresponding to infant feeding metrics and the analysis may include a so-called 'mel variational mode decomposition' or 'mel VMD'. Notably, the mel VMD may use VMD to decomposes a time-domain acoustic signal to determine a set of intrinsic mode functions (IMFs), which may be defined by amplitude-modulated and frequency-modulated components. Note that VMD may achieve noise robustness by alternating the direction method of multipliers and computing principal modes adaptively and non-recursively. In some embodiments, VMD may enable sensitivity to noise fading.

A VMD denoised signal can then be used for feature extraction or decomposition with mel-frequency cepstral coefficients (MFCC). MFCC features may capture the acoustics of the supra-glottal and sub-glottal vocal tract, thereby allowing suck and swallow sounds to be distinguished from inspiration and expiration. Moreover, the MFCC features may be combined with inertial measurement unit (IMU) and/or time-domain pressure data in an LSTM neural network to compute relevant suck, swallow and/or breathe metrics.

FIG. 22 presents a flow diagram illustrating an example of a VMD technique in accordance with an embodiment of the present disclosure.

In some embodiments, VMD may decompose (either exactly or in a least-squares sense) an original signal f(t) into a given number of modes ($\mu_k$(t), where k=1, 2, 3 . . . K and K is a non-zero integer). Thus, $$f(t) = \sum_{k=1}^{K} u_k(t)$$

where the number of modes K may be predefined. Moreover, the $\mu_k$(t) may be narrow-band mode functions, which may be expressed as $$u_k(t) = A_k(t)\cos(\phi_k(t)).$$

where $A_k(t)$ and the time derivative of a phase $\phi_k'(t)$ may be assumed to be positive and slowly varying component compared to the phase $\phi_k(t)$.

The decomposed modes may have a specific sparsity property, while reproducing the input signal. In other words, each mode may be mostly compact around a central frequency. In order to reach this goal, the bandwidth of every mode may be assessed using the following approach.

In a first operation, for each mode $\mu_k(t)$, compute the associated analytic signal by means of the Hilbert transform $$\mathcal{H}u_k(t) = \frac{1}{\pi} p \cdot v \cdot \int_{\mathbb{R}} \frac{u_k(\upsilon)}{t-\upsilon} d\upsilon$$

Then, a new analytic function $$u_k(t) + j \cdot \mathcal{H}_{t} u_k(t)$$

may be formed, which may have a unilateral frequency spectrum.

Moreover, in a second operation, shift the frequency spectrum of the mode to 'baseband' by performing mixing with an exponential function tuned to the estimated central frequency $\omega_k$ of the mode $$u_k^M = (u_k(t) + j, \mathcal{H} u_k(t)) e^{-j\omega_k t}$$

Next, the bandwidth of the inspected mode may be estimated through the H1 Gaussian smoothness of the demodulated signal or the squared L2 norm of the gradient $$BW_k = \left\| \partial_t \left[ \left( \delta(t) + \frac{j}{\pi t} \right) \times u_k(t) \right] e^{-j\omega_k t} \right\|_2^2$$

This is associated with a constrained variational problem $$\min_{u_h, \omega_k} \left\{ \sum_k \left\| \partial_t \left[ \left( \delta(t) + \frac{j}{\pi t} \right) \times u_k(t) \right] e^{-j\omega_k t} \right\|_2^2 \right\} \text{ s.t. } \sum_k u_k = f$$

In order to render the problem unconstrained, both a quadratic penalty term and Lagrangian multipliers may used to construct an augmented Lagrangian $$\mathcal{L}(u_k, \omega_k, \lambda) =$$

$$\alpha \sum_k \left\| \partial_t \left[ \left( \delta(t) + \frac{j}{\pi t} \right) \times u_k(t) \right] e^{-j\omega_k t} \right\|_2^2 + \left\| f - \sum_k u_k \right\|_2^2 + \langle \lambda, f - \sum_k u_k \rangle$$

where $\alpha$ is a parameter designed to control the bandwidth of the filter.

The resulting constrained variational problem may be solved by separate minimizations with respect to the resultant modes $\{\mu_k\}$ and their corresponding central frequencies $\{\omega_k\}$.

Based on the aforementioned approach, the VMD may be implemented as follows:

Define the number of modes K.

Initialize:

$$\{\hat{u}_k^1\},$$

$$\{\omega_k^1\},$$

$$\hat{\lambda}^1 \text{ and } n = 0.$$

Update n with n+1, and repeat the following loop:

For k=1 to K,

Update $$\hat{u}_k^{n+1}(\omega) = \frac{\hat{f}(\omega) - \sum_{i<k} \hat{u}_i^{n+1}(\omega) - \sum_{i>k} \hat{u}_i^n(\omega) + \left(\hat{\lambda}^n(\omega)/2\right)}{1 + 2a(\omega - \omega_k^n)^2}$$

for all $\omega \geq 0$ with $$\omega_k^{n+1} = \frac{\int_0^\infty \omega |\hat{u}_k^{n+1}(\omega)|^2 d\omega}{\int_0^\infty |\hat{u}_k^{n+1}(\omega)|^2 d\omega}$$

Then, perform dual ascent for all $\omega \geq 0$ $$\hat{\lambda}^{n+1}(\omega) = \hat{\lambda}^n(\omega) + \tau \left( \hat{f}(\omega) - \sum_k \hat{u}_k^{n+1}(\omega) \right)$$

until the following convergence condition is satisfied:

$$\sum_{k=1}^K \frac{\|\hat{u}_k^{n+1} - \hat{u}_k^n\|_2^2}{\|\hat{u}_k^n\|_2^2} < \varepsilon$$

where $\hat{f}$ represents the Fourier transform of original signal f(t) and $\varepsilon$ is a convergence threshold value (such as 0.05, 0.01, 1e-7, etc.).

Based on the preceding implementation, two parameters that may affect the accuracy of VMD results include: the number of modes K; and the bandwidth control parameter $\alpha$. The number of modes may be determined based at least in part on the number of frequency components contained in the signal being analyzed, while the bandwidth control parameter may be determined based at least in part on the central frequency of interest. Note that these two parameters may be related to each other. In principle, a large number of modes may result in redundant VMD information, while a small number of modes may result in mode mixing in the VMD results. Moreover, the smaller the value of bandwidth control parameter, the wider the bandwidth of the filter. When the bandwidth of the filter is wide, more background noise and interference may be included in the VMD results. However, when the filter bandwidth is too narrow, the VMD results may be distorted.

In some embodiments, the parameters used for VMD may include: a bandwidth control parameter of 5000 (which may correspond to a moderate bandwidth constraint); $\tau$ of 0

(which may indicate that a noise-tolerance of 'no strict fidelity enforcement'); a number of nodes of 6 (which may be based at least in part on a smallest error in acoustic samples); DC of 0 (or no DC part imposed); init equal to 1 (so that omegas are initialized uniformly); and tol of 1e-7 (or the tolerance of the convergence criterion). Table 1 presents pseudocode for the VMD analysis.

TABLE 1

```
# Acoustic data from the feeding session is loaded
v, sr = librosa.load(acoustic data);
gc.collect( );
# down sample the signal to match a sampling rate of pressure and
   accelerometer data
v2=scipy.signal.resample(v, len(prsw)*511, t=None, axis=0,
   window=None, domain='time');
# decompose into intrinsic mode frequencies(IMF)
sw, sw_hat, swomega = VMD(v2, alpha, tau, K, DC, init, tol);
# This results in the collection of decomposed modes (sw), the spectra
   of the modes (sw_hat) and the estimated mode center-frequencies
   (swomega).
```

FIG. 23 presents a drawing illustrating an example of acoustic measurements during feeding in accordance with an embodiment of the present disclosure. Moreover, FIG. 24 presents a drawing illustrating an example of VMD of the acoustic measurements in FIG. 23 in accordance with an embodiment of the present disclosure. Note that low-order IMFs may contain high-frequency components and they may be removed. Furthermore, higher-order IMFs may contain the low and medium frequency components and are considered as the enhanced signal. For example, the first mode may be discarded. The $2^{nd}$ mode (sw[2]) may be retained, because sucking sounds include high frequencies. Additionally, the $5^{th}$ mode (sw[5]) may be retained, because swallowing sounds include low frequencies.

Then, MFCCs may be extracted from the decomposed audio-signal modes. This approach may provide a frequency warping that better represents phonation-related sounds. Table 2 presents pseudocode for the MFCC extraction.

TABLE 2

```
SW_high=librosa.feature.mfcc(y=sw[5], sr=sr, n_mfcc=20)
SW_low=librosa.feature.mfcc(y=sw[2], sr=sr, n_mfcc=20)
```

This pseudocode may take the Fourier transform of the VMD-analyzed audio signals, filter the Fourier transformed signals through a mel bank, and then may take a logarithm of the result and apply a discrete cosine transform.

In some embodiments, the extracted outputs of the afore-mentioned analysis techniques may by input to a pretrained analysis model (such as a neural network) along with time-correlated pressure and accelerometer signals from the monitoring device to compute the feedback.

FIG. 25 presents a drawing illustrating an example of a neural network in accordance with an embodiment of the present disclosure. Notably, FIG. 25 illustrates the layers and functions in the neural network. Note that a variety of different activation functions may be used in the neural network, such as: a sigmoid or a logistic activation function, a hyberbolic tangent (tanh), a Softmax, a rectified linear unit (ReLU), a leaky ReLU, etc. In the neural network layers, note that {none} indicates that, for a three-dimensional (3D) array of input data, the batch size is not specified, which provides flexibility to accept an arbitrary batch size of data. Moreover, the second number in the triplet may represent time steps and the optional third number may be the units per sequence 1 and 44.

FIG. 26 presents a drawing illustrating an example of receiver operator characteristics for the neural network of FIG. 25 in accordance with an embodiment of the present disclosure. Table 3 summarizes the area under the receiver operator characteristic curve (AUC) for background, sucking, swallowing and breathing. Note that the neural network training dataset size may be 324,900.

TABLE 3

| | AUC |
|---|---|
| Background | 0.97 |
| Sucking | 0.98 |
| Swallowing | 0.97 |
| Breathing | 0.97 |

In some embodiments, measures of feeding integrity may be derived (e.g., using the pretrained analysis model) from the MFCCs, such as: mean, duration, frequency, rate, variation and/or sample entropy. For example, sucking, swallowing and breathing signals may be detected and assessed over time to the determine integrity of feeding skills of a baby.

In general, an index of a healthy biological systems is one that is adaptable and flexible in an unpredictable and ever-changing environment. Moreover, as part of the central patterning of aerodigestive behaviors, volitional and reflexive control mechanisms are used along with sensory feedback to modulate the timing and patterning of motor components that comprise the suck, swallow and breathe sequence.

Consequently, the sequence of oral-motor behavior during feeding over time may be reflective of central nervous system integrity. Notably, there may be a predictable pattern of motor coordination that emerges over infancy that is characterized by both stability and variability. Optimal variability may be a central feature of skills maturation. Alternatively, a lack of optimal movement variability may imply decreased adaptability of motor behavior and may be associated with abnormal sensorimotor development. For example, when there is too much variation, an infant may not be able to learn; and when there is too little variation, an infant may be stuck in immature behaviors.

In the monitoring techniques, oral motor skill deviation of an infant may be assessed using the described linear and non-linear assessments of metrics determined from the data acquired by the monitoring device. In some embodiments, an understanding of typical progression of infant skills over the neonatal period first year as motor learning shifts from a reflex to volitional control may be incorporated in the analysis. For example, FIG. 27 presents a drawing illustrating an example of variation in oral-motor behavior during development in accordance with an embodiment of the present disclosure, with optimal variability at the apex and high variation at the base of the triangular hierarchy. The trajectory of variation and entropy measures among metrics over time may be used to inform the neurological maturation of a baby. Note that atypical oral motor metrics may have related delays in shared motor behaviors, such as: aerodigestive tract, babbling and speech production. Consequently, the ability to promptly diagnose dysfunction may represent a timely opportunity for intervention.

In some embodiments, the monitoring techniques may identify incorrect equipment (such as an incorrect nipple size) and may provide corrective feedback (such as up/down in sizing, a specific size, etc.). Notably, the feeding metrics computed in the monitoring techniques may inform equipment selection based at least in part on the individual skills and/or needs of infants. In existing approaches, there typically is no guidance for parents based at least on an individual baby's feeding skills to inform parents on bottle and nipple and pacifier selection. Furthermore proper equipment may be needed to support progression of oral motor skills and to ensure safety during feeding. In the monitoring techniques, the computed feeding metrics may enable selection of an improved or optimal flow rate, nipple shape or size, and/or material from commercially available nipples. Table 4 summarizes the flow rates associated with nipples from different manufacturers.

TABLE 4

| Nipple Type | Flow Rate (mL/min) |
| --- | --- |
| Philips Avent Natural Response (2022) Level 1 (0 m) | <1 |
| Philips Avent Natural Response (2022) Level 2 (0 m+) | <1 |
| Philips Avent Natural Response (2022) Level 3 (1 m + 1) | 1 |
| Philips Avent Natural Response (2020) Level 0 (First FLow) | 2 |
| Philips Avent Natural Response (2020) Level 1 (0 m+) | 3 |
| Philips Avent Natural Response (2020) Level 2 (1 m+) | 4.5 |
| Dr. Brown's Natural Flow ® Narrow (2021) Ultra-Preemie | 4.5 |
| Tommee Tippee Closer to Nature ® (2021) Extra Slow (0 m+) | 5 |
| nfant Labs Control Flow (2021) Extra Slow (Gold) | 5 |
| Philips Avent Natural Response (2022) Level 4 (3 m+) | 6 |
| Dr. Brown's Natural Flow ® Narrow (2021) Preemie | 7 |
| Philips Avent Anti-Colic (2022) Level 1 (0 m+) | 7.5 |
| Playtex Ventaire (2017) Full Sized | 7.5 |
| Playtex Ventaire (2017) Breastlike | 7.5 |
| nfant Labs Control Flow (2021) Slow (Purple) | 8 |
| Similac ® Single-Use (2017) Slow | 8.5 |
| Dr. Brown's Natural Flow ® Narrow (2021) Preemie | 8.5 |
| Enfamil Single-Use (2019) Extra Slow | 9 |
| Playtex Naturalatch (2017) 0-3 m | 9.5 |
| Comotomo Natural Feel (2017) Slow (0-3 mo.) | 10 |
| Dr. Brown's Natural Flow ® Narrow (2021) Level T/ Newborn | 10 |
| MAM SkinSoft Silcone Teat (2021) Slow Level 0 (0 m+) | 10.25 |
| MAM SkinSoft Silcone Teat (2021) Slow Level 1 (0 m+) | 10.5 |
| nfant Labs Control Flow (2021) Standard (White) | 10.5 |
| Dr. Brown's Natural Flow ® Narrow (2021) Level 1 | 11 |
| Lansinoh NaturalWave (2022) Slow Flow | 12 |
| Enfamil Single-Use (2017) Slow | 14 |
| Gerber First Essentials (2017) Slow (0 m+) | 14 |
| Evenflo Classic (2017) Slow | 14 |
| Philips Avent Anti-Colic (2022) Level 2 (1 m+) | 14.5 |
| Dr. Brown's Natural Flow ® Narrow (2021) Level 1 | 14.5 |
| Tommee Tippee Closer to Nature ® (2021) Slow (0 m+) | 15 |
| Philips Avent Anti-Colic (2020) Level 1 (0 m+) | 16.5 |
| Similac Single-Use (2017) Standard | 18 |
| Enfamil Single-Use (2017) Standard | 19 |
| Similac Single-Use (2017) Premature | 19 |
| Legendairy Milk ® FluidFit (2022) Slow Flow | 19.5 |
| Philips Avent Natural Response (2022) Level 5 (6 m+) | |
| Medela Wide Base (2017) Slow | 22 |
| Dr. Brown's Natural Flow ® Narrow (2020) Level 2 | 23.5 |
| Philips Avent Anti-Colic (2020) Level 2 (1 m+) | 32.5 |
| Medela Calma (2017) All Stage Nipple | 37.5 |
| Dr. Brown's Natural Flow ® Narrow (2020) Level 3 | 41 |
| Dr. Brown's Natural Flow ® Narrow (2020) Level 4 | 82.5 |

In some embodiments, the monitoring techniques may facilitate the treatment of oral-motor feeding delays directly via biofeedback techniques. Notably, an application executed on the monitoring device, the electronic device and/or the computer system may suggest pacing or brief breaks to allow breathing, and/or angling of the baby bottle differently to improve infant control over milk intake. Additionally, real-time automatic pacing via an LED signal (and, more generally, the feedback) on the monitoring device may signal a parent or caregiver of a need for a feeding pause.

Note that haptic signaling may enhance cortical activation and may stimulate swallowing. Consequently, the feedback may include haptic signaling by the monitoring device to ensure safe timing of swallowing within the respiratory cycle in a close-loop manner. Moreover, aversive experiences in the hospital (such as in the neonatal intensive care unit) that are related to procedures and the abnormal sensory stimulation of frequent feeding and a breathing tube often lead to physiological dysregulation, which can exacerbate poor feeding in neonates or premature babies. Therefore, the feedback may include acoustic feedback that provides a treatment modality to assist with state regulation. Notably, the acoustic feedback may assist with infant soothing during feeding by use maternal vocal-derived audio signals (e.g., using a generative neural network) to generate predictable rhythms and high-melodic contours that entrain infant physiological stability and provide improved or optimal state regulation for feeding. This acoustic feedback (such as rhythmic stimuli) may help infants have more coordinated and more synchronized motor behaviors.

In some embodiments, treatments or treatment recommendations based at least in part on oral-motor metrics that are computed in the monitoring techniques may include individualized pacifiers and/or nipples that address functional and anatomical deficits to provide graduated improvement of oral motor strength and growth, including lip, jaw, tongue and/or coordination of movements for improved or optimal development. Existing nipples and pacifiers may interact with the palate differently based at least in part on their dimensions and materials in conjunction with the infant's anatomy. Using the measurements from our assessment device, finite element analysis may be used to evaluate the effects that size, geometry, relative positions, loads and/or materials have on the resulting feeding forces, pressures, and/or total contact area between the pacifier or nipple and the palate. Graduated feeding equipment may also be used to transition from bottle to breast feeding and vice versa in a baby who is not able to do so otherwise because of behavioral or skill-related refusals. In addition to assisting motor and adaptive skills development, appropriate-sized nipple and/or pacifier use may be a protective factor in sudden infant death syndrome, and improved or optimally designed nipples and/or pacifiers may assist with improved or optimal airway stabilization via this protective effect.

We now discussed different feeding scenarios and examples of the feedback that may be provided in the monitoring techniques. For example, based at least in part on the computed feeding metrics, a poor latch may be detected (such as from weak suction pressure at baseline). In response, the feedback may recommend: a longer, narrow-based nipple; and/or a pacifier with wide shield. Alternatively, ankyglossia or a tongue tie may be detected from: weak compression pressure; and/or the time between maximum compression and swallowing. In response, the feedback may recommend: follow up with an ear-nose-and-throat specialist or a pediatrician; and/or using silicone instead of a latex nipple. Moreover, a disorganized suck, swallow and breathe sequence or pattern may include: increased sucks and swallows; and/or a high coefficient of variation in measured sucks and swallows. In response, the feedback may recommend: a side-lying baby bottle angle guidance; and decreasing a flow rate of a nipple: Furthermore, in response to an increased swallow/breathe rate, the feedback may recommend a decreased nipple flow rate. Additionally, in response to poor suction pressure during feeding, the feedback may recommend use of a high-compliance pacifier.

In some embodiments, in the first days to months when a premature baby is home from the hospital, there may be long feedings with low volume. The baby may have one or more symptoms: turning away from the breast or a baby bottle; sucking for a few minutes, then refuses to drink anymore; refusing to close their mouth around the nipple; screaming when placed into a feeding position; gagging or fussing as the nipple nears their mouth; and/or chewing on the nipple.

The monitoring techniques may be used to assess and provide feedback to help address one or more of these problems. Notably, in the monitoring techniques, a suck, swallow and breathe sequence of pattern may be assessed, including suck, swallow and breathe bursts and/or pauses. Then, based at least in part on analysis of the measurements, the feedback may provide specific recommendations and/or general feeding tips for skill improvement or optimization. For example, the feedback may include recommendations, such as: positioning; supporting the head/shoulders in midline; flexion of upper extremities and lower extremities; a suitable environment (such as low stimulation); and/or calming techniques. Note that real-time feedback (e.g., during feeding) may be provided using the monitoring device and/or the electronic device, while feedback after the feeding may be provided via the electronic device.

In one example, the measurements performed by the monitoring device may indicate a high variation in a suck, swallow and breathe pattern. For example, a coefficient of variation in suck-to-swallow may be greater than 0.45. In response, the feedback may include: an indication of how to hold the baby bottle at the correct angle (such as a dynamically illuminated green LED when the baby bottle is at the correct angle); and/or a real-time proactive or reactive pacing light (such as a dynamically illuminated red LED to indicate when to pace) on the monitoring device for when time to pace. Notably, when proactive pacing, the feedback may include setting the baby on their side briefly after 3-5 sucks. Alternatively, when reactive pacing, the feedback may be to give the baby a 1-2 min. break from the feeding when there are signs of fatigue or irregular respiration. In some embodiments, the feedback may be provided after the feeding and/or in real-time during the feeding. Note that in some embodiments, the feedback may include a recommendation to use a slower flow nipple or to use an optional infant flow-control device enhancement in the monitoring device.

In a second example, the measurements performed by the monitoring device may indicate a high suck-to-breathe ratio. For example, there may not be sufficient breaths, such as a burst of five or more sucks without breathing. When this occurs, the feedback may be similar to that in the first example. Notably, the feedback, which may be provided after the feeding and/or in real-time during the feeding, may include: instructions for pacing or regulation, a recommendation to use a slower flow nipple, or to use an optional infant flow-control device enhancement in the monitoring device. In some embodiments, the feedback may include to set the baby on their side after 3-5 sucks or to use automatic pacing.

In a third example, the measurements performed by the monitoring device may indicate a timing of suck to breath. For example, a coefficient of variation in suck-to-breath timing may be greater than 0.3 and/or there may be less than 40% breath-swallow coupling in an inspiration, swallow and expiration pattern. In response, the feedback may include: advice to follow up with a pediatrician regarding a need for a swallowing study; instructions for pacing; and instructions to decrease the flow rate.

In a fourth example, the measurements performed by the monitoring device may indicate a high suck-to-swallow ratio or excessive pressure while the flow rate is too slow. For example, the suck-to-swallow ratio may be greater than four, the pressure may be greater than 180 mm Hg and/or the suction pressure may be greater than 100 mm Hg. In response, the feedback may include a recommendation or instruction to increase the nipple flow rate. Note that the feedback may be provided after the feeding and/or in real-time during the feeding.

In a fifth example, the measurements performed by the monitoring device may indicate a high suck rate with weak pressure during feeding and/or a low volume intake. For example, the suck rate may be greater than 70/min. with a pressure during feeding of less than 40 mm Hg and/or with a low volume intake. In response, the feedback may include: a recommendation for jaw support; a recommendation for pacifier strengthening skills with a pacifier between feedings; and/or a recommendation to switch to a softer nipple. Notably, the recommendation may include using a small baby bottle so they can hold it and still provide jaw and cheek support. Then, when a suck pattern is established, they may gently try to pull the nipple from the baby's mouth to promote stronger sucking. Note that the feedback may be provided after the feeding and/or in real-time during the feeding.

In a sixth example, the measurements performed by the monitoring device may indicate weak sucking pressure with high volume intake. These feeding metrics may be associated with a so-called 'compression feeder' or an infant that uses their tongue for compression (as opposed to using their mouth for suction). For example, a compression feeder may have a different between a suck and a swallow pressure of less than 40 mm Hg. In response, feedback may include: a recommendation to provide cheek pressure assistance; a recommendation to use an infant directed flow; a recommendation to change a nipple shape; and/or a recommendation to use a pacifier. Note that the feedback may be provided after the feeding and/or in real-time during the feeding.

In a seventh example, the measurements performed by the monitoring device may indicate: a fast suck rate (such as greater than 60 per second), a clicking sound during feeding, decreased movement of the tongue (e.g., a compression pressure less than 30 mm Hg) and/or weak suction pressure (e.g., less than 40 mm Hg). In response, real-time feedback may include pacing recommendations or instructions. Alternatively or additionally, after the feeding, the feedback may include: a recommendation to follow up with a healthcare provider about possible ankyglossia; a recommendation regarding cheek pressure; and/or a recommendation regarding pacifier use.

In an eighth example, the measurements performed by the monitoring device may indicate: discomfort during feed, rejecting a baby bottle and/or arching. For example, a suck, swallow and breath pattern may be variable (such as a covariance greater than 0.5). Moreover, there may be: sucking pressure changes and/or gulping sounds during feeding. In response, the feedback may include: a possible diagnosis of aerophagia (which may be associated with weak latch/suction pressure and/or a fast flow rate leading to gulping). Notably, real-time feedback may include: instructions for pacing; and/or a recommendation to use rhythmic vibration or stimulation of the baby. Furthermore, after the feeding, the feedback may include: a recommendation to adjust a feeding position; a recommendation to decrease the flow rate; a recommendation to use an improved or optimal post-feeding positioning; and/or when there is a decreased swallow frequency, a recommendation to follow up with a healthcare provider regarding possible acid reflux.

In a nineth example, after a diagnosis of reflux and the use of proton pump inhibitors, the measurements performed by the monitoring device may indicate that a baby may still be fussy during feeding; and/or a suck, swallow and breath pattern may have irregularities in swallowing. These feeding metrics may be associated with aerophagia. Alternatively or additionally, the measurements performed by the monitoring device may indicate a low oral motor tone, such as: a suck pressure less than 50 mm Hg; and/or a compression pressure less than 20 mm Hg. These feeding metrics may be associated with Down syndrome or another cause of low tone associated with weak strength and coordination skills. Real-time feedback may include: a recommendation for pacing or regulation; a recommendation to provide jaw or cheek support; and/or a recommendation to use rhythmic vibration or stimulation of the baby. In addition to possible diagnostic information, after the feeding the feedback may include: advice on pacing; a recommendation to use a nipple with a slower flow rate; a recommendation to use a flow-control device enhancement; a recommendation to adjust a feeding position; and/or a recommendation to facilitate flexion with a chin-tuck position to increase sucking skill.

In a tenth example, along with a history of poor weight gain, the measurements performed by the monitoring device may indicate: arhythmic sucking and breathing; and/or short suck bursts with long pauses. In response, the real-time feedback may include: a recommendation for pacing; and/or a recommendation for rhythmic vibration or stimulation of the baby. Moreover, after the feeding, the feedback may include: pacing information; a recommendation for an improved or optimal nipple; a recommendation to follow up with a healthcare provider to consider the impact of cardio-respiratory system on feeding; and/or a recommendation to enable pauses or to use more-frequent feeding to make up for reduced aerobic capacity.

In an eleventh example, there may be a diagnosis of Down syndrome or another cause of low tone associated with weak strength and coordination skills. In response, the real-time feedback may include: a recommendation for pacing or regulation; and/or a recommendation for jaw or cheek support. Moreover, after the feeding, the feedback may include: advice on pacing; a recommendation to use a nipple with a slower flow rate; a recommendation to use a flow-control device enhancement; and/or a recommendation to facilitate flexion with a chin-tuck position to increase sucking skill.

In a twelfth example, a baby may have been feeding well for a few months, but now may be increasingly fussy during feedings. Notably, the feedings may take a longer amount of time and may require more work. The measurements performed by the monitoring device may indicate an irregular suck, swallow and breath pattern. These feeding metrics may be associated with or may indicate colic with aerophagia. In response, the real-time feedback may include: a recommendation for pacing or regulation; and/or a recommendation for rhythmic vibration or stimulation of the baby.

In a thirteenth example, a 6-month old may gag on pureed food and may not be able to advance solids. The monitoring device may be used to assess a suck, swallow and breathe pattern. In response, the real-time feedback may include a recommendation for rhythmic vibration or stimulation of the baby. Moreover, after the feeding, the feedback may include: advice on pacing; a recommendation for an improved or optimal nipple; and/or recommendations or tips for oral-motor maturation.

In a fourteenth example, there may be concerns about the overall development of a 4-month old. The monitoring device may be used to assess a suck, swallow and breathe pattern to determine the adaptability from feeding to feeding. For example, the feeding metrics may indicate that a coefficient of variation decreases toward 3-4 months and, then instead of stabilizing, continues to decrease to less than 0.35. After feeding, the feedback may include: a maturation score; recommendations or tips for development; a recommendation for occupation, physical or feeding therapy; and/or a recommendation to follow up with a healthcare provide, such as a pediatrician.

We now describe additional embodiments of the analysis techniques. In some embodiments, the analysis techniques may: be based solely on audio measurements (and, thus, may provide audio-alone capabilities); or detect breath constituents (inhale/exhale), as well as suck, swallow and breathe pattern(s); or detect safe swallow-breathe patterns based at least in part on a timing of inhale suck and swallow. Note that while infants have been used as an illustrative example in the preceding discussion, the analysis techniques may be used in children and/or adults.

As discussed previously, feeding coordination, which involves the proper timing between sucking/chewing, swallowing, and breathing, is important for infants and adults. Swallowing is a complicated process that involves precise coordination of various muscles and nerves. It is a vital function that allows us to consume food and liquids. The timing of inspiration (breathing in) and expiration (breathing out) plays an important role in ensuring safe swallowing.

Typically, swallowing occurs during the expiratory phase of the respiratory cycle. This means that we usually swallow while we are breathing out. This timing helps to ensure that the airway is closed when food or liquid is passing through the pharynx, reducing the risk of aspiration.

Aspiration refers to the entry of food, liquid, or other material into the lungs, which can lead to serious complications, such as pneumonia. A major defense against aspiration is the coordination of swallowing and breathing, where swallowing typically occurs during a brief pause in breathing known as apnea. This coordination is often disrupted in individuals with swallowing disorders or dysphagia.

In healthy individuals, swallowing usually occurs during the expiratory phase of respiration (exhalation). After swallowing, respiration resumes with another exhalation. This pattern is called 'exhale-swallow-exhale' and it helps prevent aspiration by ensuring that the airway is clear of food or liquid before and after swallowing. In babies the maturation of this pattern unfolds in a predictable manner.

However, in infants, children or adults with neurological disorders or dysphagia, this coordination can be disrupted, leading to swallows that occur during inhalation or that are followed by inhalation ('inhale-swallow-inhale' or 'exhale-swallow-inhale'). This can increase the risk of aspiration because the breath following the swallow can draw food or liquid into the lungs.

By identifying swallow timing in relation to inspiration and expiration, the disclosed analysis techniques may allow healthcare providers to assess an individual's risk of aspiration and to plan appropriate interventions. These interventions may include techniques to improve swallow-respiration coordination, changes in diet texture or consistency, or the use of postures that can help protect the airway during swallowing.

Preterm or neurologically compromised infants may face issues such as aspiration because of poor coordination, while irregular swallowing coordination in adults may indicate underlying neurodegenerative conditions like Parkinson's or dementia. Current approaches to assess feeding coordination are typically limited and often invasive. Therefore, there is a need for non-invasive techniques for monitoring and assessing feeding coordination.

In the disclosed analysis techniques, a monitoring device, an electronic device and/or a computer system may use a microphone, advanced signal processing techniques, a processor, and/or a pretrained analysis model to monitor feeding coordination by analyzing audio signals. One or more of these components may be used with infants and/or adults. Notably, one or more of the components may identify irregular patterns in feeding coordination, which may indicate risks or underlying neurological conditions.

In some embodiments, the monitoring device may include a microphone and an application-based platform to non-invasively record feeding sounds. The sound may be produced by or associated with variations in air pressure. In this case, the sounds of interest may be produced during the feeding cycle of an infant, including sounds of inhaling, exhaling, swallowing, and sucking. When these sounds are represented as variations with respect to time (t), they may form a sound signal. The extraction of information from these complicated sounds may be performed by converting the sound into analog or digital signal form. For example, the conversion into the first spectrogram (waveform representation) may be performed using a sound signaling process. Each feeding sound may have a different periods and amplitudes because they belong to different categories, and this may result in unique spectrograms. Consequently, the spectrograms may be used to discriminate between the different feeding sounds based at least in part on their pattern and behavior. The wave period (T) and frequency (f) may be expressed as $$f = \frac{1}{T} \tag{1}$$

and $$T = \frac{1}{f}. \tag{2}$$

Moreover, the velocity (v) may be expressed in terms of the frequency and the wavelength ($\lambda$) as $$v = f \cdot \lambda. \tag{3}$$

Rearranging Eqn. 3 yields $$f = v \cdot \lambda. \tag{4}$$

From Eqns. 2 and 4, the time period may be expressed in terms of the velocity and wavelength as $$T = \frac{\lambda}{v}. \tag{5}$$

The processor may first denoises the audio signal(s) using VMD. As discussed previously, VMD is a signal processing technique that may be used to decompose a signal into a set of intrinsic mode functions. In this case, VMD may be applied to the feeding sounds to decompose them into their constituent modes. This decomposition may help to isolate the different types of sounds (inhale, exhale, swallow, suck) from background noise and may reduce the complexity of the signal.

Then, the process may segment the denoised signals into distinct suck, swallow, and breath events based at least in part on their signal profiles. The denoised signals may be passed to a feature extraction module (or set of instructions), which may use MFCCs to obtain characteristics (such as duration, peaks, and/or shape) of the events. MFCCs may provide a compact representation of the power spectrum of an audio signal. These features may capture the characteristics of the feeding sounds and may be used as inputs to a pretrained analysis model.

Moreover, the extracted MFCCs may be fed into a convolutional neural network or CNN (which is an example of a pretrained analysis model) for classification. CNNs are a type of machine-learning model (e.g., a deep learning model) that are effective for processing grid-like data, such as time-series data or images. In this case, the CNN may be trained to classify the different types of feeding sounds (inhale, exhale, swallow, suck) based at least in part on the MFCCs. These features may then be fed into a CNN that classifies each event as suck, swallow, or breath(inhale and exhale).

A coordination identification module (or set of instructions) may analyze the sequences and timing between the classified events to determine rhythms and patterns. Any irregularities in these patterns may be flagged, which may indicate aspiration risk in infants and/or adults. In addition, any irregularities in the patterns may indicate coordination dysfunction that may be linked to neurodevelopmental and neurological processes.

The monitoring device may enable non-invasive monitoring of feeding coordination in infants and/or adults using only audio signals and advanced signal processing techniques. It may identify irregular breathing and swallowing patterns that may reflect underlying health issues, allowing for early intervention and diagnosis.

In some embodiments, the monitoring device that monitors feeding coordination is described. The monitoring device may include: a microphone that records feeding audio signals; a processor that denoises and segments capture audio signals into distinct suck, swallow and breath events using VMD; and a CNN that classifies the events based at least in part on MFCCs associated with the audio signals; and an analysis module that identifies irregular coordination patterns in the audio signals.

Note that the irregular patterns may indicate potential aspiration risk in infants (e.g., a child less than 1-year old). Moreover, the irregular patterns may indicate a potential neurological condition in an adult (such as an individual older than 18 years).

Furthermore, the CNN may be trained using annotated feeding audio data.

Another embodiment provides a computer-readable storage medium for use with the monitoring device. When executed by the monitoring device, this computer-readable storage medium causes the monitoring device to perform at least some of the aforementioned operations.

Another embodiment provides a method, which may be performed by the monitoring device. This method includes at least some of the aforementioned operations. For example, the monitoring device may monitor feeding coordination and/or may identify risks or conditions.

Note that the monitoring device may allow healthcare providers to non-invasively assess or perform: early diagnosis; treatment planning; monitoring progress; and/or prevention of serious complications. For example, in early diagnosis, the monitoring device may detect irregular suck-swallow-breathe (SSB) patterns that may facilitate early identification of infants who may have feeding disorders, even before overt signs such as poor weight gain or respiratory problems appear. This may enable early intervention and may prevent potential complications. Moreover, in treatment planning, the monitoring device may provide detailed information about the specific aspects of SSB coordination that an infant is struggling with. This may help a clinician or a healthcare provider tailor feeding therapies. For example, when an infant is having difficulty coordinating sucking and swallowing, targeted therapies may be used to improve this specific skill.

Furthermore, in monitoring progress, the monitoring device may provide an ongoing assessment of SSB patterns that may be used to monitor an infant's progress in response to therapy. This may help in making necessary adjustments to the treatment plan. Additionally, in prevention of serious complications, the monitoring device may provide a precise understanding of the SSB coordination that may help prevent serious complications, such as aspiration, which can lead to pneumonia. By recognizing a baby's or an adult's inability to coordinate these actions, a caregiver or a healthcare provider may employ strategies, such as specific feeding positions, specialized feeding bottles, or slower feeding rates, to reduce the risk of aspiration.

The quantitative monitoring of swallow-breath timing using the monitoring device may provide a window into sensorimotor development underlying feeding maturation in infancy or in an adult. This capability may enable earlier supportive interventions when needed. In contrast with existing assessment techniques, the disclosed analysis techniques may be non-invasive and lower-cost, and may not involve radiation exposure risks.

We now describe embodiments of a computer, which may perform at least some of the operations in the monitoring techniques. FIG. 28 presents a block diagram illustrating an example of an electronic device 2800, e.g., monitoring device 110, electronic device 112, access points 116, radio node 118, switch 128 and/or a computer or server in computer system 130, in accordance with some embodiments. For example, electronic device 2800 may include: processing subsystem 2810, memory subsystem 2812, and networking subsystem 2814. Processing subsystem 2810 includes one or more devices configured to perform computational operations. For example, processing subsystem 2810 can include one or more microprocessors, ASICs, microcontrollers, programmable-logic devices, GPUs and/or one or more DSPs. Note that a given component in processing subsystem 2810 are sometimes referred to as a 'computation device'.

Memory subsystem 2812 includes one or more devices for storing data and/or instructions for processing subsystem 2810 and networking subsystem 2814. For example, memory subsystem 2812 can include dynamic random access memory (DRAM), static random access memory (SRAM), and/or other types of memory. In some embodiments, instructions for processing subsystem 2810 in memory subsystem 2812 include: program instructions or sets of instructions (such as program instructions 2822 or operating system 2824), which may be executed by processing subsystem 2810. Note that the one or more computer programs or program instructions may constitute a computer-program mechanism. Moreover, instructions in the various program instructions in memory subsystem 2812 may be implemented in: a high-level procedural language, an object-oriented programming language, and/or in an assembly or machine language. Furthermore, the programming language may be compiled or interpreted, e.g., configurable or configured (which may be used interchangeably in this discussion), to be executed by processing subsystem 2810.

In addition, memory subsystem 2812 can include mechanisms for controlling access to the memory. In some embodiments, memory subsystem 2812 includes a memory hierarchy that comprises one or more caches coupled to a memory in electronic device 2800. In some of these embodiments, one or more of the caches is located in processing subsystem 2810.

In some embodiments, memory subsystem 2812 is coupled to one or more high-capacity mass-storage devices (not shown). For example, memory subsystem 2812 can be coupled to a magnetic or optical drive, a solid-state drive, or another type of mass-storage device. In these embodiments, memory subsystem 2812 can be used by electronic device 2800 as fast-access storage for often-used data, while the mass-storage device is used to store less frequently used data.

Networking subsystem 2814 includes one or more devices configured to couple to and communicate on a wired and/or wireless network (i.e., to perform network operations), including: control logic 2816, an interface circuit 2818 and one or more antennas 2820 (or antenna elements). (While FIG. 28 includes one or more antennas 2820, in some embodiments electronic device 2800 includes one or more nodes, such as antenna nodes 2808, e.g., a metal pad or a connector, which can be coupled to the one or more antennas 2820, or nodes 2806, which can be coupled to a wired or optical connection or link. Thus, electronic device 2800 may or may not include the one or more antennas 2820. Note that the one or more nodes 2806 and/or antenna nodes 2808 may constitute input(s) to and/or output(s) from electronic device 2800.) For example, networking subsystem 2814 can include a Bluetooth™ networking system, a cellular networking system (e.g., a 3G/4G/5G network such as UMTS, LTE, etc.), a USB networking system, a networking system based on the standards described in IEEE 802.11 (e.g., a Wi-Fi® networking system), an Ethernet networking system, and/or another networking system.

Networking subsystem 2814 includes processors, controllers, radios/antennas, sockets/plugs, and/or other devices used for coupling to, communicating on, and handling data and events for each supported networking system. Note that mechanisms used for coupling to, communicating on, and handling data and events on the network for each network system are sometimes collectively referred to as a 'network interface' for the network system. Moreover, in some embodiments a 'network' or a 'connection' between electronic devices does not yet exist. Therefore, electronic device 2800 may use the mechanisms in networking subsystem 2814 for performing simple wireless communication between electronic devices, e.g., transmitting advertising or beacon frames and/or scanning for advertising frames transmitted by other electronic devices.

Within electronic device 2800, processing subsystem 2810, memory subsystem 2812, and networking subsystem 2814 are coupled together using bus 2828. Bus 2828 may include an electrical, optical, and/or electro-optical connection that the subsystems can use to communicate commands and data among one another. Although only one bus 2828 is shown for clarity, different embodiments can include a different number or configuration of electrical, optical, and/or electro-optical connections among the subsystems.

In some embodiments, electronic device 2800 includes a display subsystem 2826 for displaying information on a display, which may include a display driver and the display, such as a liquid-crystal display, a multi-touch touchscreen, etc. Moreover, electronic device 2800 may include a user-interface subsystem 2830, such as: a mouse, a keyboard, a trackpad, a stylus, a voice-recognition interface, and/or another human-machine interface.

Electronic device 2800 can be (or can be included in) any electronic device with at least one network interface. For example, electronic device 2800 can be (or can be included in): a desktop computer, a laptop computer, a subnotebook/netbook, a server, a supercomputer, a tablet computer, a smartphone, a smartwatch, a cellular telephone, a consumer-electronic device, a portable computing device, communication equipment, a monitoring device and/or another electronic device.

Although specific components are used to describe electronic device 2800, in alternative embodiments, different components and/or subsystems may be present in electronic device 2800. For example, electronic device 2800 may include one or more additional processing subsystems, memory subsystems, networking subsystems, and/or display subsystems. Additionally, one or more of the subsystems may not be present in electronic device 2800. Moreover, in some embodiments, electronic device 2800 may include one or more additional subsystems that are not shown in FIG. 28. Also, although separate subsystems are shown in FIG. 28, in some embodiments some or all of a given subsystem or component can be integrated into one or more of the other subsystems or component(s) in electronic device 2800. For example, in some embodiments program instructions 2822 are included in operating system 2824 and/or control logic 2816 is included in interface circuit 2818.

Moreover, the circuits and components in electronic device 2800 may be implemented using any combination of analog and/or digital circuitry, including: bipolar, PMOS and/or NMOS gates or transistors. Furthermore, signals in these embodiments may include digital signals that have approximately discrete values and/or analog signals that have continuous values. Additionally, components and circuits may be single-ended or differential, and power supplies may be unipolar or bipolar.

An integrated circuit may implement some or all of the functionality of networking subsystem 2814 and/or electronic device 2800. The integrated circuit may include hardware and/or software mechanisms that are used for transmitting signals from electronic device 2800 and receiving signals at electronic device 2800 from other electronic devices. Aside from the mechanisms herein described, radios are generally known in the art and hence are not described in detail. In general, networking subsystem 2814 and/or the integrated circuit may include one or more radios.

In some embodiments, an output of a process for designing the integrated circuit, or a portion of the integrated circuit, which includes one or more of the circuits described herein may be a computer-readable medium such as, for example, a magnetic tape or an optical or magnetic disk or solid state disk. The computer-readable medium may be encoded with data structures or other information describing circuitry that may be physically instantiated as the integrated circuit or the portion of the integrated circuit. Although various formats may be used for such encoding, these data structures are commonly written in: Caltech Intermediate Format (CIF), Calma GDS II Stream Format (GDSII), Electronic Design Interchange Format (EDIF), OpenAccess (OA), or Open Artwork System Interchange Standard (OASIS). Those of skill in the art of integrated circuit design can develop such data structures from schematics of the type detailed above and the corresponding descriptions and encode the data structures on the computer-readable medium. Those of skill in the art of integrated circuit fabrication can use such encoded data to fabricate integrated circuits that include one or more of the circuits described herein.

While some of the operations in the preceding embodiments were implemented in hardware or software, in general the operations in the preceding embodiments can be implemented in a wide variety of configurations and architectures. Therefore, some or all of the operations in the preceding embodiments may be performed in hardware, in software or both. For example, at least some of the operations in the monitoring techniques may be implemented using program instructions 2822, operating system 2824 (such as a driver for interface circuit 2818) or in firmware in interface circuit 2818. Thus, the monitoring techniques may be implemented at runtime of program instructions 2822. Alternatively or additionally, at least some of the operations in the monitoring techniques may be implemented in a physical layer, such as hardware in interface circuit 2818.

In the preceding description, we refer to 'some embodiments'. Note that 'some embodiments' describes a subset of all of the possible embodiments, but does not always specify the same subset of embodiments. Moreover, note that the numerical values provided are intended as illustrations of the monitoring techniques. In other embodiments, the numerical values can be modified or changed.

The foregoing description is intended to enable any person skilled in the art to make and use the disclosure, and is provided in the context of a particular application and its requirements. Moreover, the foregoing descriptions of embodiments of the present disclosure have been presented for purposes of illustration and description only. They are not intended to be exhaustive or to limit the present disclosure to the forms disclosed. Accordingly, many modifications and variations will be apparent to practitioners skilled in the art, and the general principles defined herein may be applied to other embodiments and applications without departing from the spirit and scope of the present disclosure. Additionally, the discussion of the preceding embodiments is not intended to limit the present disclosure. Thus, the present disclosure is not intended to be limited to the embodiments shown, but is to be accorded the widest scope consistent with the principles and features disclosed herein.

What is claimed is:

1. A monitoring device, comprising a housing, wherein the housing comprises:

a first connector configured to mechanically couple to a baby bottle;

a second connector configured to mechanically couple to a nipple;

a tube having a first opening defined by a first edge proximate to the first connector and a having second opening defined by a second edge proximate to the second connector; and a set of sensors configured to perform measurements associated with feeding, wherein the monitoring device is configured to:

perform the measurements while a baby is performing the feeding, wherein the measurements are associated with sucking, swallowing and breathing by the baby, and wherein the set of sensors comprise an acoustic sensor and an inertial measurement unit, a pressure sensor, or both, and the measurements comprise measurements in an acoustic band of frequencies between 50-20,000 Hz; and dynamically provide feedback based at least in part on a modal decomposition of mel-frequency cepstral coefficients (MFCC) corresponding to at least a portion of the measurements and an output from a pretrained neural network that uses the measurements as an input, wherein the modal decomposition comprises variational mode decomposition (VMD) of at least the portion of the measurements, wherein the feedback comprises: when to dynamically pause the feeding, a change to a flow rate during the feeding, a change to a size of the nipple, a change to a size of the baby bottle, a change to promote stronger sucking by the baby, a change to an anatomical position of the baby during the feeding, a recommendation for a swallowing study, a recommendation for the baby to use a pacifier between instances of the feeding, diagnostic information about a possible tongue-tie, diagnostic information about possible excessive air swallowing into the stomach or a recommendation for additional therapy for the baby.

2. The monitoring device of claim 1, wherein the feedback comprises: signals or instructions to guide a feeder to regulate a number of sucks per burst or sequence of swallows, a respiratory rate or a duration of bursts and pauses or time intervals between swallows by adjusting a flow rate dial, an angle of the baby bottle or both.

3. The monitoring device of claim 1, wherein at least the portion of the measurements correspond to acoustics of the supra-glottal and sub-glottal vocal tract and the pretrained neural network is configured to distinguish suck and swallow sounds from inspiration and expiration.

4. The monitoring device of claim 1, wherein pretrained analysis model comprises a neural network.

5. The monitoring device of claim 1, wherein the monitoring device comprises an interface circuit configured to wirelessly communicate with an electronic device, which is separate from the monitoring device; and wherein the monitoring device is configured to:

provide, addressed to the electronic device, information associated with the measurements; and may receive the feedback associated with the electronic device.

6. The monitoring device of claim 1, wherein the monitoring device is configured to provide the feedback about a quality of the feeding while the baby is feeding.

7. The monitoring device of claim 1, wherein the monitoring device comprises an integrated circuit configured to analyze the measurements, determine the feedback, or both.

8. The monitoring device of claim 1, wherein the set of sensors comprise: an accelerometer, a light detection and ranging (LiDAR) sensor or an infrared sensor.

9. The monitoring device of claim 1, wherein the feedback corresponds to or comprises one or more oral-motor metrics and the one or more oral-motor metrics comprise: tongue kinetics, a force of sucking, a suction and expression pressure, a flow rate, a sucking/swallowing/breathe ratio, micro-gagging, a pressure of lip seal, a pressure of tongue, or a distance from the monitoring device to a top of a fluid level line of the baby bottle.

10. The monitoring device of claim 1, wherein the feedback comprises diagnostic information associated with possible feeding/oromotor difficulties.

11. The monitoring device of claim 10, wherein the diagnostic information comprises a feeding performance score.

12. The monitoring device of claim 10, wherein the diagnostic information comprises: possible developmental delays or possible feeding difficulties.

13. The monitoring device of claim 12, wherein the possible feeding difficulties comprise: reflux, colic, or a type of oral-motor functional impairment.

14. The monitoring device of claim 1, wherein the feedback comprises one or more feeding quality metrics and the one or more feeding quality metrics comprise: oral pressure, feeding consistency, or a sucking/swallowing/breath rate.

15. The monitoring device of claim 1, wherein the feedback comprises a normalized maturity index corresponding to a ratio of a developmental metrics of the baby and a chronological age of the baby.

16. A non-transitory computer-readable storage medium for use in conjunction with a monitoring device configured to couple to a baby bottle and a nipple, the monitoring device comprising a set of sensors configured to perform measurements associated with feeding, the computer-readable storage medium configured to store program instructions that, when executed by the monitoring device, causes the monitoring device to perform one or more operations comprising:

performing, using the set of sensors, the measurements associated with the feeding while a baby is performing the feeding, wherein the measurements are associated with sucking, swallowing and breathing by the baby, and wherein the set of sensors comprise an acoustic sensor and an inertial measurement unit, a pressure sensor, or both, and the measurements comprise measurements in an acoustic band of frequencies between 50-20,000 Hz; and dynamically providing feedback based at least in part on a modal decomposition of mel-frequency cepstral coefficients (MFCC) corresponding to at least a portion of the measurements and an output from a pretrained neural network that uses the measurements as an input, wherein the modal decomposition comprises variational mode decomposition (VMD) of at least the portion of the measurements, wherein the feedback comprises: when to dynamically pause the feeding, a change to a flow rate during the feeding, a change to a size of a nipple, a change to a size of a baby bottle, a change to promote stronger sucking by the baby, a change to an anatomical position of the baby during the feeding, a recommendation for a swallowing study, a recommendation for the baby to use a pacifier between instances of the feeding, diagnostic information about a possible tongue-tie, diagnostic information about possible excessive air swallowing into the stomach or a recommendation for additional therapy for the baby.

17. The non-transitory computer-readable storage medium of claim 16, wherein at least the portion of the measurements correspond to acoustics of the supra-glottal and sub-glottal vocal tract and the pretrained neural network distinguishes suck and swallow sounds from inspiration and expiration.

18. A method for providing feedback, comprising:

by a monitoring device coupled to a baby bottle and a nipple, the monitoring device comprising a set of sensors that perform measurements associated with feeding:

performing, using the set of sensors, the measurements associated with the feeding while a baby is performing the feeding, wherein the measurements are associated with sucking, swallowing and breathing by the baby, and wherein the set of sensors comprise an acoustic sensor and an inertial measurement unit, a pressure sensor, or both, and the measurements comprise measurements in an acoustic band of frequencies between 50-20,000 Hz; and dynamically providing feedback based at least in part on a modal decomposition of mel-frequency cepstral coefficients (MFCC) corresponding to at least a portion of the measurements and an output from a pretrained neural network that uses the measurements as an input, wherein the modal decomposition comprises variational mode decomposition (VMD) of at least the portion of the measurements, wherein the feedback comprises: when to dynamically pause the feeding, a change to a flow rate during the feeding, a change to a size of a nipple, a change to a size of a baby bottle, a change to promote stronger sucking by the baby, a change to an anatomical position of the baby during the feeding, a recommendation for a swallowing study, a recommendation for the baby to use a pacifier between instances of the feeding, diagnostic information about a possible tongue-tie, diagnostic information about possible excessive air swallowing into the stomach or a recommendation for additional therapy for the baby.

19. The method of claim 18, wherein at least the portion of the measurements correspond to acoustics of the supra-glottal and sub-glottal vocal tract and the pretrained neural network distinguishes suck and swallow sounds from inspiration and expiration.

20. The method of claim 18, wherein the feedback comprises: signals or instructions to guide a feeder to regulate a number of sucks per burst or sequence of swallows, a respiratory rate or a duration of bursts and pauses or time intervals between swallows by adjusting a flow rate dial, an angle of the baby bottle or both.

* * * * *